United States Patent
Gong

(10) Patent No.: US 11,072,578 B2
(45) Date of Patent: Jul. 27, 2021

(54) TRANSMEMBRANE PORES FORMED BY AROMATIC OLIGOAMIDE FOLDAMERS AND USES OF SAME

(71) Applicant: The Research Foundation for The State University of New York, Amherst, NY (US)

(72) Inventor: Bing Gong, Amherst, NY (US)

(73) Assignee: The Research Foundation for The State University of New York, Amherst, NY (US)

(*) Notice: Subject to any disclaimer, the term of this patent is extended or adjusted under 35 U.S.C. 154(b) by 0 days.

(21) Appl. No.: 16/801,648

(22) Filed: Feb. 26, 2020

(65) Prior Publication Data

US 2020/0199066 A1 Jun. 25, 2020

Related U.S. Application Data

(63) Continuation of application No. PCT/US2018/061325, filed on Nov. 15, 2018.

(60) Provisional application No. 62/729,235, filed on Sep. 10, 2018, provisional application No. 62/586,589, filed on Nov. 15, 2017.

(51) Int. Cl.
| | |
|---|---|
| *C07C 237/42* | (2006.01) |
| *A61K 47/69* | (2017.01) |
| *A61K 9/127* | (2006.01) |
| *B82Y 5/00* | (2011.01) |

(52) U.S. Cl.
CPC .......... *C07C 237/42* (2013.01); *A61K 9/1274* (2013.01); *A61K 9/1277* (2013.01); *A61K 47/6919* (2017.08); *B82Y 5/00* (2013.01)

(58) Field of Classification Search
None
See application file for complete search history.

(56) References Cited

U.S. PATENT DOCUMENTS 6,495,680 B1 12/2002 Gong

FOREIGN PATENT DOCUMENTS

WO 2018/035496 A1 2/2018

OTHER PUBLICATIONS

Longitudinal. (1992). In C. G. Morris (Ed.), Academic Press Dictionary of Science and Technology (4th ed.). Elsevier Science & Technology. Credo Reference: https://search.credoreference.com/content/entry/apdst/longitudinal/0?institutionId=743 (Year: 1992).*
Yamamoto ("Cavity-containing, backbone-rigidified foldamers and macrocycles" Chem. Commun., 2012, 48, p. 12142-12158) (Year: 2012).*

(Continued)

*Primary Examiner* — Amy C Bonaparte
(74) *Attorney, Agent, or Firm* — Hodgson Russ LLP

(57) ABSTRACT

Provided are aromatic oligoamide foldamers and self-assembled compositions of the same. The aromatic oligoamide foldamers and compositions can form tube-like structures that can form pores in membranes. The pores can be used to transport ions and molecules, such as, for example, cryoprotective agents or therapeutic agents, through the membrane. The tube-like structures exhibit desirable stability at low temperatures.

12 Claims, 5 Drawing Sheets

(a) 
B series (b) 
N series (c) 
BN series

*n* = 1 and other integers

R = alkyl (e.g., methyl, ethyl, propyl, ...octyl and other longer and branched) group
or
oligoether [e.g., -(CH$_2$)$_2$OCH$_3$, -(CH$_2$)$_2$OCH$_2$CH$_3$, -(CH$_2$)$_2$OCH$_2$CH(CH$_3$)$_2$, -(CH$_2$)$_2$O(CH$_2$)$_2$CH(CH$_3$)$_2$] group X = CH$_3$CO-, CF$_3$CO-, PhCH$_2$CO-,  and other acyl groups Y = -HNCH$_3$, -HNCH$_2$CH$_3$, -HNR (R = alkyl), -HNAr (Ar = aryl)
or
-OCH$_3$, -OCH$_2$CH$_3$, -OC(CH$_3$)$_3$, OR (R = alkyl)

(56) References Cited

OTHER PUBLICATIONS

Gong 2018 ("Effects of Oligomer Length, Solvents, and Temperature on the Self-Association of Aromatic Oligoamide Foldamers" Organic Letters, 2018, 20, p. 5486-5489). (Year: 2018).*
Prabhakaran ("Sterically controlled naphthalene homo-oligoamides with novel structural architectures" Organic and Biomolecular Chemistry, 2009, 7, p. 2458-2465) (Year: 2009).*
Zou ("Tunable Mesogens Based on Shape-Persistent Aromatic Oligoamides: From Lamellar, Columnar, to Nematic Liquid Crystalline Phase" Organic Letters, 2012, 14, p. 3584-3587) (Year: 2012).*
https://en.wikipedia.org/wiki/Molecule, downloaded on Jul. 17, 2020 (Year: 2020).*
Gong, B. and Shao, Z., Self-Assembling Organic Nanotubes with Precisely Defined, Sub-nanometer Pores: Formation and Mass Transport Characteristics, Accounts of Chemical Research, Apr. 18, 2013, vol. 46, No. 12, pp. 2856-2866.
Wu, X., et al., Discrete Stacking of Aromatic Oligoamide Macrocycles, Journal of the American Chemical Society, Apr. 24, 2015, vol. 137, pp. 5879-5882.

* cited by examiner

A

64mer

TRANSMEMBRANE PORES FORMED BY AROMATIC OLIGOAMIDE FOLDAMERS AND USES OF SAME

CROSS REFERENCE TO RELATED APPLICATIONS

This application is a continuation of International Patent Application No. PCT/US2018/061325, filed on Nov. 15, 2018, which claims priority to U.S. Provisional Application No. 62/586,589, filed on Nov. 15, 2017, and to U.S. Provisional Application No. 62/729,235, filed on Sep. 10, 2018, the disclosures of which are hereby incorporated by reference.

FIELD OF THE DISCLOSURE

The disclosure generally relates to oligoamide foldamers. More particularly the disclosure relates to self-assembling aromatic oligoamide foldamers that can be used to form transmembrane pores.

BACKGROUND OF THE DISCLOSURE

The plasma membrane plays a vital biological role by serving as a permeability barrier that prevents unassisted movement of most water-soluble substances. This membrane maintains the characteristic differences between the inside and outside of the cell. In biological systems, the permeability of cell membrane is regulated by passive pores driven along, and by active transporters against, the concentration gradient.

Efforts to create synthetic channels started three decades ago and are still ongoing, with the majority of systems being based on ion transport and few on molecular transport. Compared to protein pores, synthetic organic pores offer unique advantages including substantially smaller molecular masses, synthetic tunability allowing the incorporation of structural units that otherwise are incompatible with or cannot be incorporated into protein-based pores, high stability and non-immunogenicity. However, due to the limitations of current synthetic methods, the architectural variability of membrane proteins remains widely unexplored and inaccessible to synthetic constructs. In fact, large functional pores that can be readily synthesized with minimal help from biological approaches are remarkably rare.

The controlled poration of plasma membranes can revolutionize many important applications related to the transport of impermeable hydrophilic substances across cell membranes. The use of natural pore-forming proteins for intracellular delivery of hydrophilic molecules such as sugars has shown promise. It was previously demonstrated that intracellular delivery of 0.2 M trehalose significantly improved post-thaw cell viability when transported through a genetically engineered variant of the pore forming toxin, α-hemolysin. The large lumen of α-hemolysin (14 Å) can allow sufficient transport of molecules like trehalose, but replaces adverse CPA cytotoxicity with cytotoxicity based-upon a lack of selective transport due to a large pore that remained opened, especially at physiological temperature. A rational blockage strategy was critical to reduce toxicity and the genetically engineered pore forming protein based on α-hemolysin was blocked with addition high concentrations of $Zn^{2+}$ ion for 18 hours. Besides, most biological pores suffer from thermal and mechanical instability, incompatibility with solvents other than water, and immunogenicity. Overcoming the deficiencies of protein pores by developing synthetic pores capable of mimicking natural systems has attracted the interest of many chemists over the last several decades. These channels and pores provide significant advantages such as synthetic efficiency and structure diversity to engineer various functions such as responsiveness and selective transport. With their ready functionalization, versatile compatibility, and modular molecular recognition, organic nanotubes, which can be structurally modified, could overcome the limits of biological and known synthetic pores. Most known systems of synthetic pores developed thus far are focused on selective ion transport with few capable of transporting molecules. Self-assembling or unimolecular pores with sizes that allow the transport of molecules, especially membrane-impermeable hydrophilic molecules, are few, while synthetic pores that are modulated by external stimuli such pH, light, or heat are not yet available.

SUMMARY OF THE DISCLOSURE

The present disclosure provides aromatic oligoamide foldamers and self-assembled compositions formed from aromatic oligoamide foldamers. Compounds and compositions can form tube-like structures that can form pores in membranes. The present disclosure also provides uses of the compounds and compositions of the present disclosure.

In an aspect, the present disclosure provides compounds comprising folding oligoamides (folding oligoamides are also referred to herein as "foldamers"). Oligoamides comprise a plurality of aromatic substituents linked by at least one amide bond.

In an example, the compounds of the present disclosure have a curved backbone. Not intending to be bound by any particular theory, the curved backbone is largely due to intramolecular hydrogen bonds that rigidify the amide linkage of each amide group to each aromatic substituent and at least in part to an interaction between the aromatic substituents (e.g., π-π interactions), whereby the curved backbone is stabilized.

In various examples, an aromatic substituent of the present disclosure has the following structure:

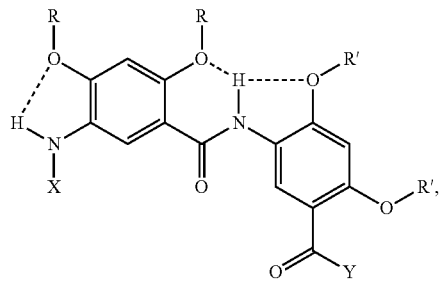

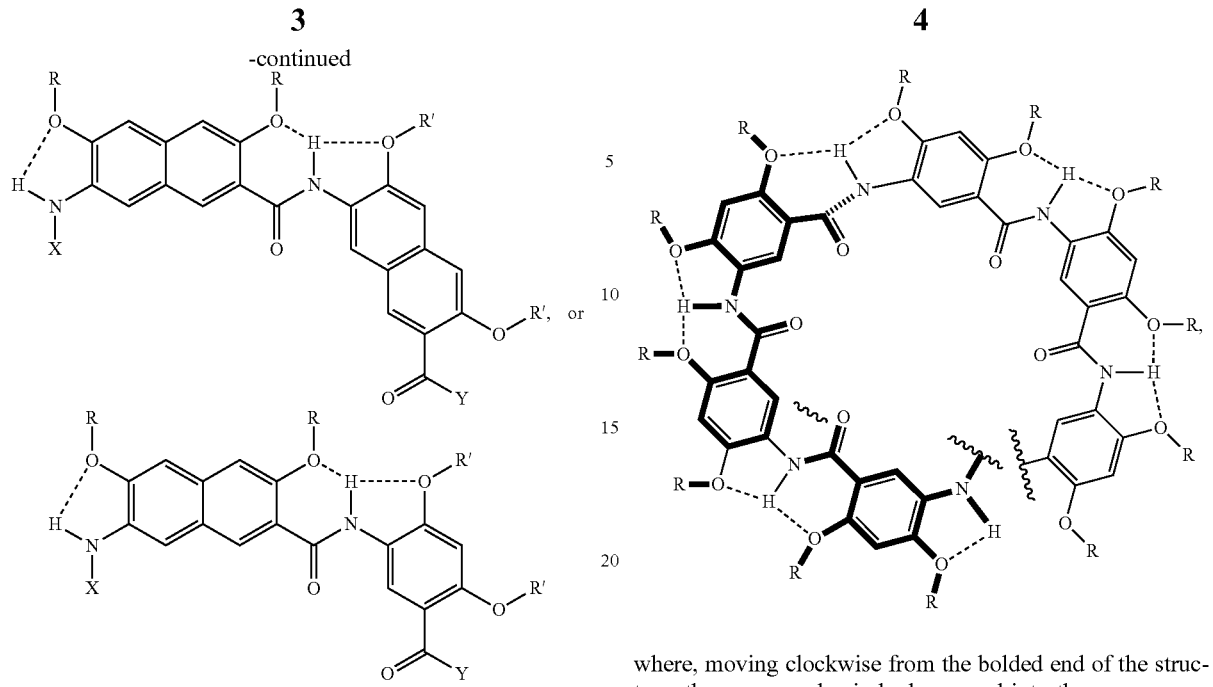

(hereinafter "B," "N," and "BN" residues, respectively), where R and R' are independently selected from the group consisting of linear alkyl (e.g., methyl, ethyl, propyl, butyl, pentyl, hexyl, heptyl, octyl groups, and the like) groups, branched alkyl groups (e.g., branched derivatives of propyl, butyl, pentyl, hexyl, heptyl, octyl groups, and the like) and ether groups and oligoether groups (e.g., —(CH$_2$)$_2$OCH$_3$, —(CH$_2$)$_2$OCH$_2$CH$_3$, —(CH$_2$)$_2$OCH$_2$CH(CH$_3$)$_2$, —(CH$_2$)$_2$O(CH$_2$)$_2$CH(CH$_3$)$_2$, and the like); X is an acyl group (e.g., acetyl, trifluoroacetyl, phenylacetyl, fluorenylmethyloxycarbonyl, and the like) or an aryl substituent; and Y is i) —NHCH$_3$, —NHCH$_2$CH$_3$, —NHR", or —NHAr, ii) —OCH$_3$, —OCH$_2$CH$_3$, —OCH$_2$CH$_3$, —OC(CH$_3$)$_3$, or OR", where Ar is an aryl group and R" is a linear or branched alkyl group (e.g., methyl, ethyl, propyl, butyl, pentyl, hexyl, heptyl, octyl groups, and the like), or an aromatic substituent.

Additional examples of oligoether groups include, but are not limited to,

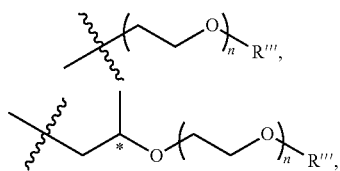

and the like, where the asterisk denotes a stereogenic carbon (i.e., a carbon having R or S stereochemistry), n is 1, 2, 3, 4, 5, or 6, and R''' is a linear or branched alkyl group (e.g., methyl, ethyl, propyl, isopropyl, and the like).

In an example, compounds of the present disclosure form folded, tube-like structures (e.g., a helix). In a non-limiting illustrative example, the compound folds as shown in the following structure (using the B aromatic substituent as an example, and not excluding examples of N, BN, and combinations thereof (including combinations with B)):

where, moving clockwise from the bolded end of the structure, the compound spirals downward into the page.

In an aspect, the present disclosure provides compositions comprising compounds of the present disclosure. In an example, a plurality of compounds of the present disclosure assemble such that the compounds are stacked atop one another to form a cylindrical structure. The cylindrical structure is a composition of assembled compounds and the longitudinal axis of each compound is coaxially aligned. The cylindrical structure has an interior and an exterior. The interior of cylindrical structure is a continuously hollow tubular cavity. Other assemblies are contemplated and are within the scope of the subject invention.

A composition of the present disclosure can form a helix (and accordingly can be referred to as a helix or helical composition). A helix can be right-handed or left-handed.

In an aspect, the present disclosure provides uses of compounds and/or compositions of the present disclosure. In various examples, a compound or compounds and/or composition of the present disclosure are used to form pores in a vesicle (e.g., transmembrane pores in a liposome and/or cell). The pores can be nanopores. In various examples, compounds and/or compositions of the present disclosure can be administered to cells, tissues, organs, or an individual (e.g., an individual in need thereof). The individual may be a human, a non-human mammal, a non-mammalian animal or a plant.

The compounds and/or compositions of the present disclosure can form transmembrane pores. For example, the membrane is a membrane of a liposome, a cell, or other similar vesicle or molecular system. Compounds and/or compositions of the present disclosure can be referred to as pore-forming compounds and/or compositions.

A molecule of interest can be transported through a pore (e.g., transmembrane pore) formed by compounds and/or compositions of the present disclosure. In various examples, a molecule of interest is a hydrophilic species. Accordingly, in various examples, a method of the present disclosure comprises contacting a membrane of a vesicle (e.g., a liposome and/or cell or similar system) having a transmembrane pore with a molecule of interest, where the molecule of interest is transported into the vesicle (e.g., a liposome and/or cell or similar system). In various other examples, a molecule of interest (e.g., a hydrophilic species) is transported out of a cell. Non-limiting examples of molecules of interest include ions (e.g., protons, sodium, potassium, or chloride ions), dyes (e.g., 8-hydroxypyrene-1,3,6-trisulfonic acid trisodium salt (HPTS)), nutrients typically used in cell or tissue culture, small molecules (e.g., drugs, such as, for example, the anticancer drug, 5-Fluoro-2'-deoxyuridine (5-FdU), and the like), carbohydrates (e.g., pentoses and hexoses, such as, for example, but not limited to, mannose, glucose, galactose, and the like; disaccharides such as, but not limited to, sucrose and trehalose, and the like), polyhydric alcohols (also referred to herein as "sugar alcohols," such as, for example, mannitol, sorbitol, and the like), sequestration agents of metal ions (e.g., hydrophilic sequestration agents of metal ions, such as, for example, hydrophilic sequestration agents of Fe(II) and/or Fe(III)), cryoprotective agents (CPAs, such as, for example, but not limited to, DMSO, ethylene glycol, and propylene glycol), peptides, and combinations thereof. Examples of suitable CPAs, ions, and nutrients are known in the art.

A method for using compounds and/or compositions of the present disclosure comprises i) contacting a membrane of a vesicle (e.g., a liposome, cell, or similar vesicle or molecular system), where the vesicle optionally encapsulates a stimuli-responsive molecule (e.g., a fluorescent dye), with at least one compound and/or composition of the present disclosure such that the compound and/or composition form a pore in the membrane of the vesicle; ii) contacting an analyte (e.g., a solution comprising an analyte, such as, for example, a carbohydrate, a peptide, a dye, and/or an ion) with the vesicle such that the analyte interacts (e.g., binds) with the pore; and iii) measuring a change in fluorescence emission of the encapsulated stimuli-responsive molecule.

In an aspect, a compound and/or composition of the present disclosure can be used in a method for molecular-level chromatography.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
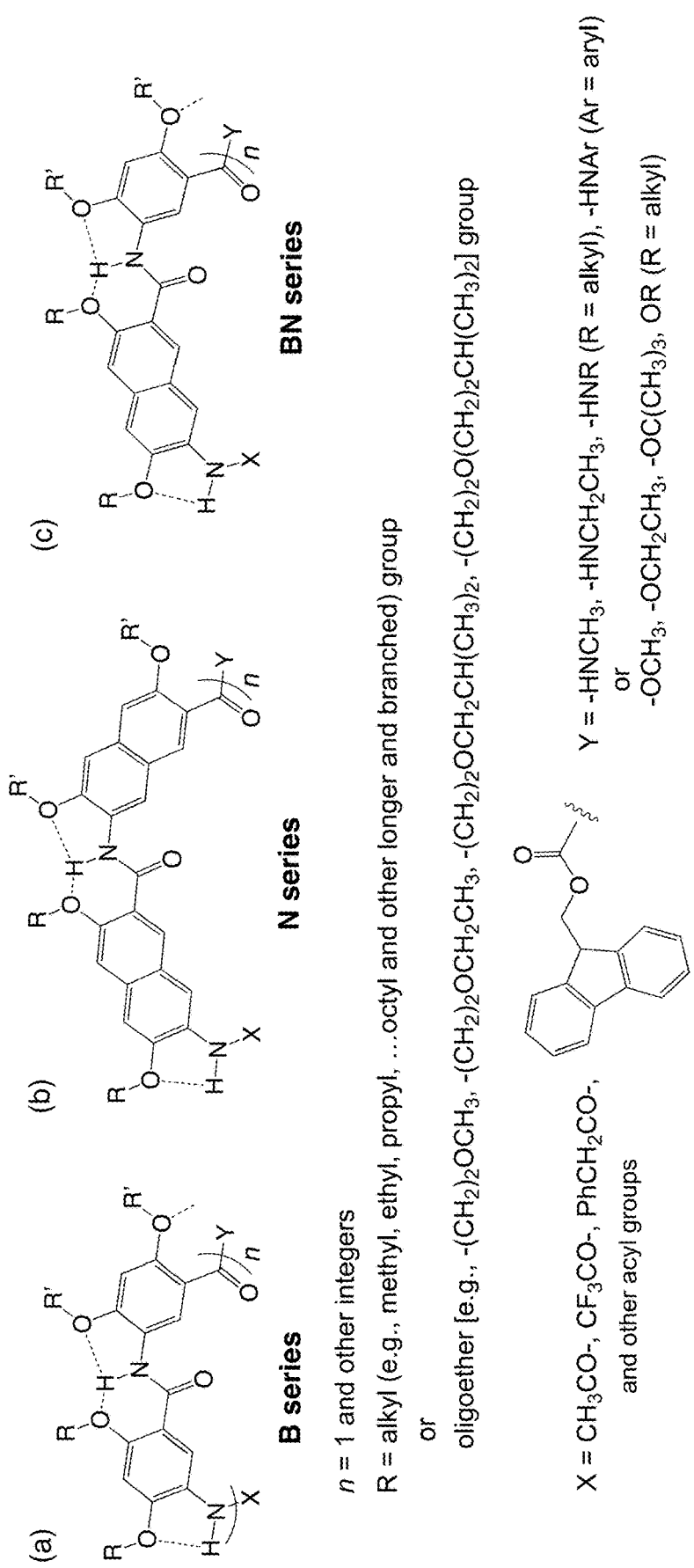
FIG. 1 shows three series of aromatic oligoamides that fold into helical conformations containing inner pores of different diameter.

Although claimed subject matter will be described in terms of certain examples, other examples, including examples that do not provide all of the benefits and features set forth herein, are also within the scope of this disclosure. Various structural, logical, process step, and electronic changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

As used herein, unless otherwise stated, the term "group" refers to a chemical entity that has one terminus that can be covalently bonded to other chemical species. Examples of groups include, but are not limited to:

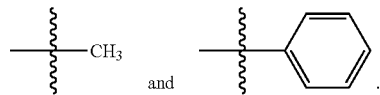

As used herein, unless otherwise stated, the term "moiety" refers to a chemical entity that has two or more termini that can be covalently bonded to other chemical species. Examples of moieties include, but are not limited to:

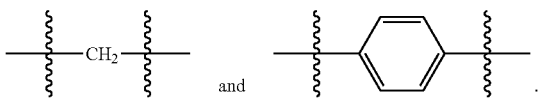

As used herein, unless otherwise indicated, the term "alkyl" refers to branched or unbranched saturated hydrocarbon groups. Examples of alkyl groups include, but are not limited to, methyl groups, ethyl groups, propyl groups, butyl groups, isopropyl groups, tert-butyl groups, and the like. For example, the alkyl group can be a $C_1$ to $C_{12}$ alkyl group, including all integer numbers of carbons and ranges of numbers of carbons therebetween ($C_1$, $C_2$, $C_3$, $C_4$, $C_5$, $C_6$, $C_7$, $C_8$, $C_9$, $C_{10}$, $C_{11}$, and $C_{12}$). The alkyl group can be unsubstituted or substituted with one or more substituent. Examples of substituents include, but are not limited to, various substituents such as, for example, halogens (—F, —Cl, —Br, and —I), aliphatic groups (e.g., alkyl groups, alkenyl groups, alkynyl groups), aryl groups, alkoxide groups, carboxylate groups, carboxylic acids, ether groups, amines, alcohols, thiols, and the like, and combinations thereof.

As used herein, unless otherwise indicated, the term "aryl" refers to $C_5$ to $C_{14}$ aromatic or partially aromatic carbocyclic groups, including all integer numbers of carbons and ranges of numbers of carbons therebetween ($C_5$, $C_6$, $C_7$, $C_8$, $C_9$, $C_{10}$, $C_{11}$, $C_{12}$, $C_{13}$, and $C_{14}$). The aryl group can comprise polyaryl moieties such as, for example, fused rings or biaryl moieties. The aryl group can be unsubstituted or substituted with one or more substituent. Examples of substituents include, but are not limited to, various substituents such as, for example, halogens (—F, —Cl, —Br, and —I), aliphatic groups (e.g., alkenes, alkynes), aryl groups, alkoxides, carboxylates, carboxylic acids, ether groups, amines, alcohols, thiols, and the like, and combinations thereof. Examples of aryl groups include, but are not limited to, phenyl groups, biaryl groups (e.g., biphenyl groups), and fused ring groups (e.g., naphthyl groups).

The compounds and compositions of the subject invention can be used in cryoprotection, nanopore-facilitated transport and/or uptake of therapeutic molecules (or drug delivery) and/or other pharmaceutical or biological applications. For example, the compounds and compositions can be used in drug delivery by releasing the contents of capsules like liposomes, biotherapeutics by permeabilizing cells to cytotoxic drugs, or biopreservation by loading cells with bioprotective agents.

The present disclosure provides aromatic oligoamide foldamers and self-assembled compositions formed from aromatic oligoamide foldamers. Compounds and compositions can form tube-like structures that can form pores in membranes. The present disclosure also provides uses of the compounds and compositions of the present disclosure.

In an aspect, the present disclosure provides compounds comprising folding oligoamides (folding oligoamides are also referred to herein as "foldamers"). Oligoamides comprise a plurality of aromatic substituents linked by at least one amide bond.

In an example, the compounds of the present disclosure have a curved backbone. Not intending to be bound by any particular theory, the curved backbone is largely due to intramolecular hydrogen bonds that rigidify the amide linkage of each amide group to each aromatic substituent and at least in part to an interaction between the aromatic substituents (e.g., π-π interactions), whereby the curved backbone is stabilized.

In various examples, an aromatic substituent of the present disclosure has the following structure:

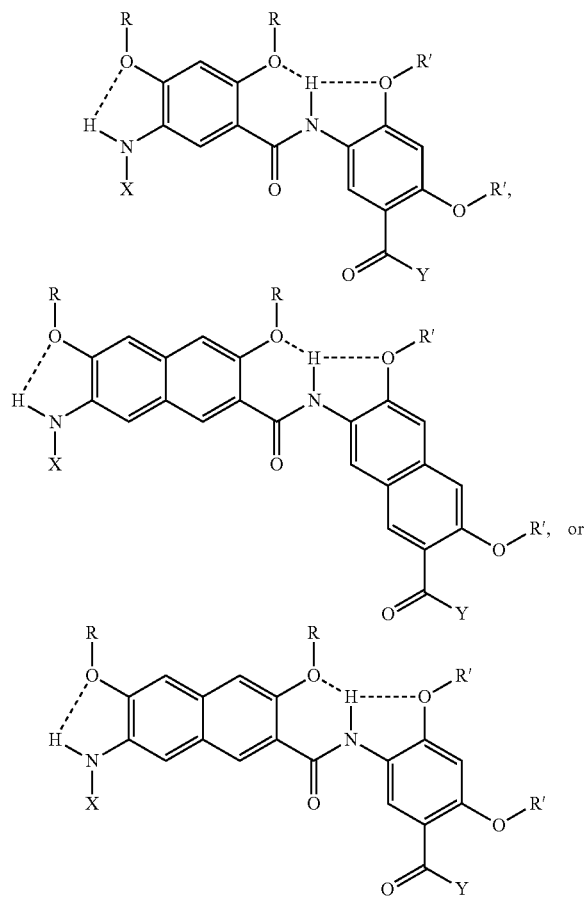

(hereinafter "B," "N," and "BN" residues, respectively), where R and R' are independently selected from the group consisting of linear alkyl (e.g., methyl, ethyl, propyl, butyl, pentyl, hexyl, heptyl, octyl groups, and the like) groups, branched alkyl groups (e.g., branched derivatives of propyl, butyl, pentyl, hexyl, heptyl, octyl groups, and the like) and ether groups and oligoether groups (e.g., —(CH$_2$)$_2$OCH$_3$, —(CH$_2$)$_2$OCH$_2$CH$_3$, —(CH$_2$)$_2$OCH$_2$CH(CH$_3$)$_2$, —(CH$_2$)$_2$O(CH$_2$)$_2$CH(CH$_3$)$_2$, and the like); X is an acyl group (e.g., acetyl, trifluoroacetyl, phenylacetyl, fluorenylmethyloxycarbonyl, and the like) or an aryl substituent; and Y is i) —NHCH$_3$, —NHCH$_2$CH$_3$, —NHR", or —NHAr, ii) —OCH$_3$, —OCH$_2$CH$_3$, —OCH$_2$CH$_3$, —OC(CH$_3$)$_3$, or —OR", where Ar is an aryl group and R" is a linear or branched alkyl group (e.g., methyl, ethyl, propyl, butyl, pentyl, hexyl, heptyl, octyl groups, and the like), or an aromatic substituent.

Additional examples of oligoether groups include, but are not limited to,

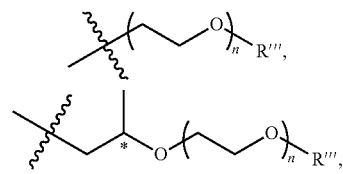

and the like, where the asterisk denotes a stereogenic carbon (i.e., a carbon having R or S stereochemistry), n is 1, 2, 3, 4, 5, or 6, and R''' is a linear or branched alkyl group (e.g., methyl, ethyl, propyl, isopropyl, butyl, isobutyl, t-butyl, pentyl, neopentyl, isopentyl, and the like).

A compound can have various numbers of aromatic substituents (e.g., aryl moieties such as B, N, and BN residues). In an example, a compound has 1 to 128 aromatic substituents, including all integer number of aromatic substituents. In various examples, a compound is a 8mer, 10mer, 12mer, 16mer, 32mer, 64mer, or 128mer, where the integer (e.g., 8, 16, etc.) corresponds to the number of aromatic substituents (e.g., aryl moieties such as B, N, and/or BN residues) in the compound.

In an example, a compound of the present disclosure has the following structure:

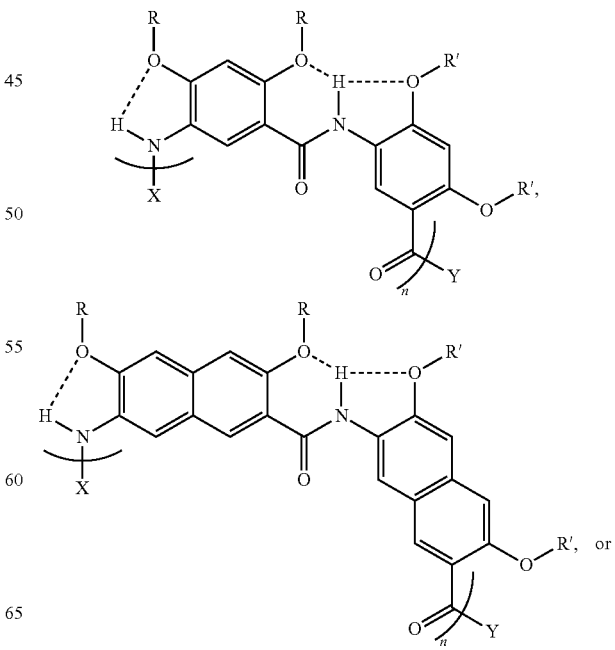

-continued

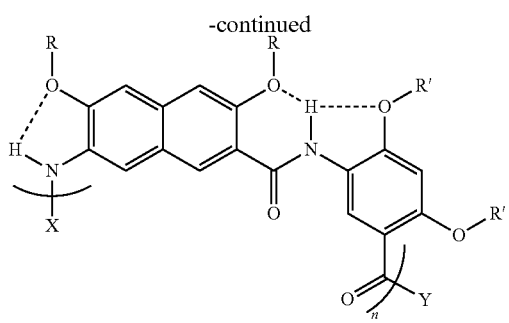

(hereinafter "B," "N," and "BN" residues, respectively), where R and R' are independently selected from the group consisting of linear alkyl (e.g., methyl, ethyl, propyl, butyl, pentyl, hexyl, heptyl, octyl groups, and the like) groups, branched alkyl groups (e.g., branched derivatives of propyl, butyl, pentyl, hexyl, heptyl, octyl groups, and the like) and ether groups and oligoether groups (e.g., —(CH$_2$)$_2$OCH$_3$, —(CH$_2$)$_2$OCH$_2$CH$_3$, —(CH$_2$)$_2$OCH$_2$CH(CH$_3$)$_2$, —(CH$_2$)$_2$O(CH$_2$)$_2$CH(CH$_3$)$_2$, and the like); X is an acyl group (e.g., acetyl, trifluoroacetyl, phenylacetyl, fluorenylmethyloxycarbonyl groups, and the like); Y is i) —NHCH$_3$, —NHCH$_2$CH$_3$, —NHR", or —NHAr or ii) —OCH$_3$, —OCH$_2$CH$_3$, —OCH$_2$CH$_3$, —OC(CH$_3$)$_3$, or —OR", where Ar is an aryl group and R" is a linear or branched alkyl group (e.g., methyl, ethyl, propyl, butyl, pentyl, hexyl, heptyl, octyl groups, and the like); and where n=1 to 64, including all integers and ranges therebetween. In various examples, n is 4, 5, 6, 7, 8, 9, 10, 11, 12, 13, 14, 15, 16, 17, 18, 19, or 20. In various examples, n is 4, 5, or 6.

In an example, a compound of the present disclosure, for each aromatic substituent, at least one substituent (e.g., R and/or R') of the aromatic substituent that is bonded to an oxygen and hydrogen bonded to an amide hydrogen must be a methyl group. For example, for each backbone amide linkage, at least one substituent on the aromatic substituents on either side of the amide linkage (e.g., R and/or R') must be a methyl group.

In various examples, each substituent (e.g., R and/or R') on an aromatic substituent can be the same, different, or a combination of various substituents. In non-limiting illustrative examples, the aromatic substituents of a compound of the present disclosure has one of the following structures:

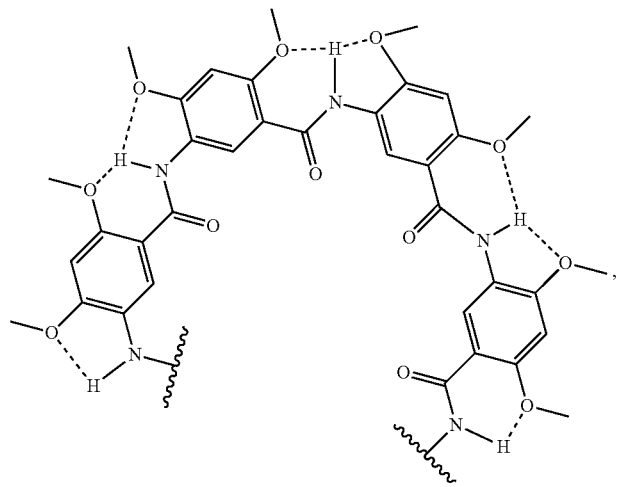

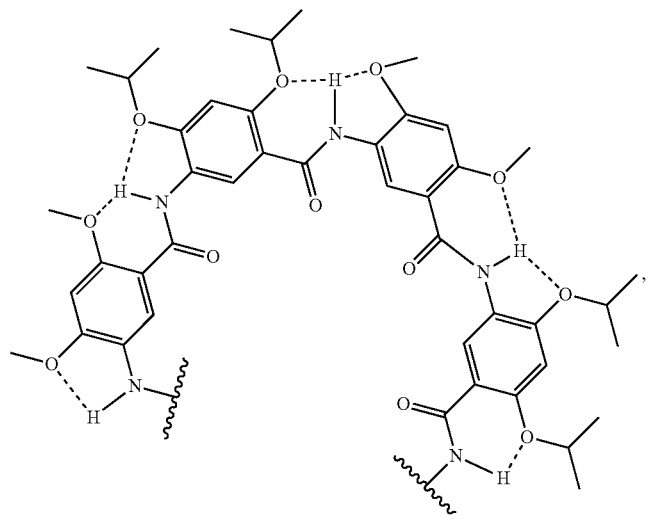

-continued
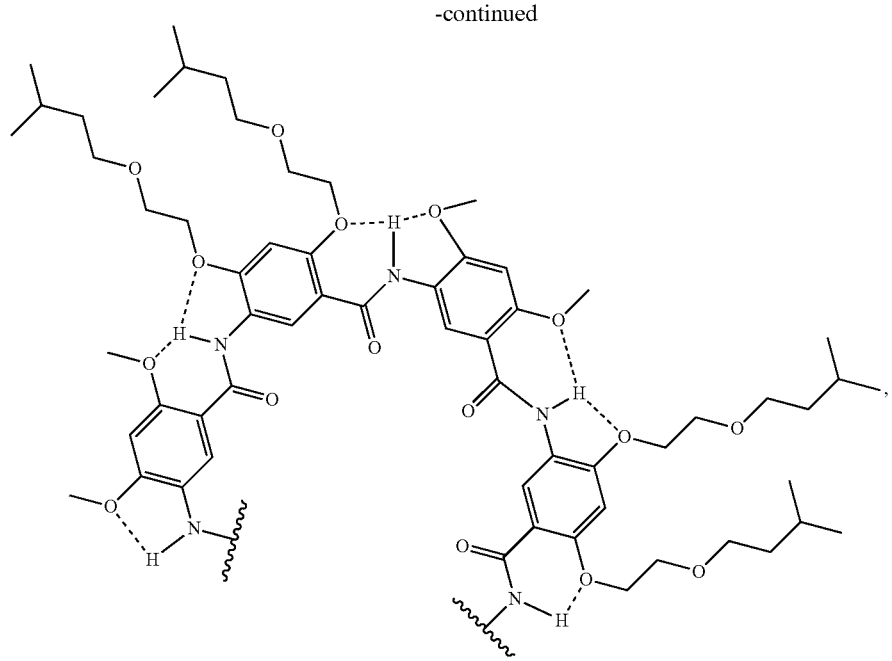
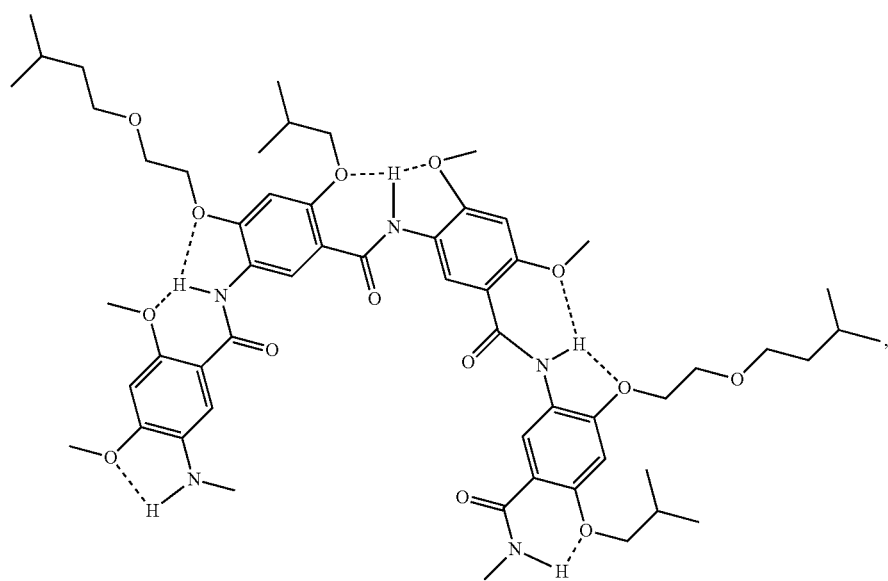

-continued
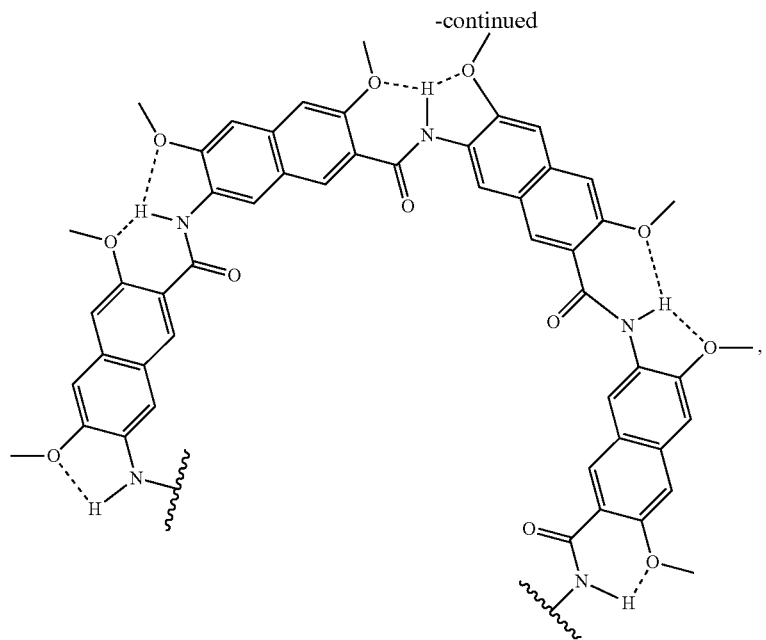
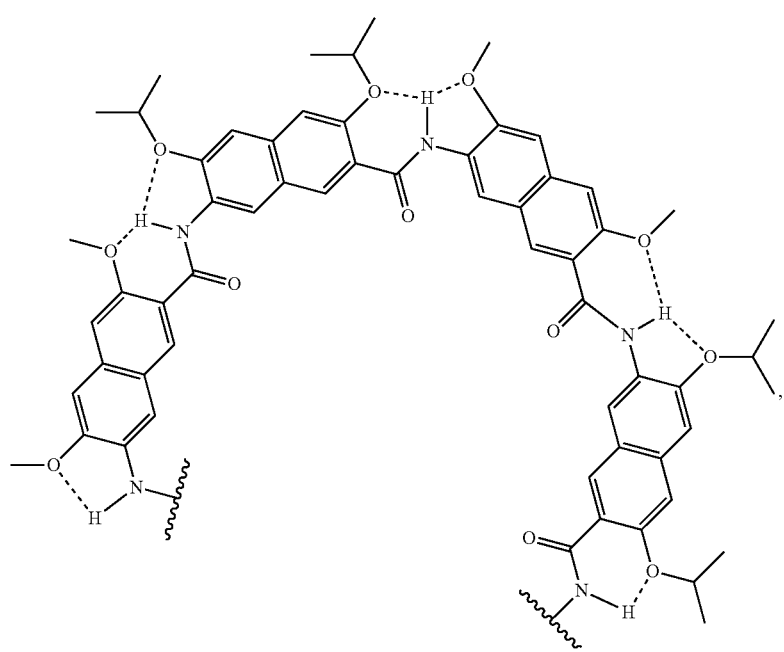

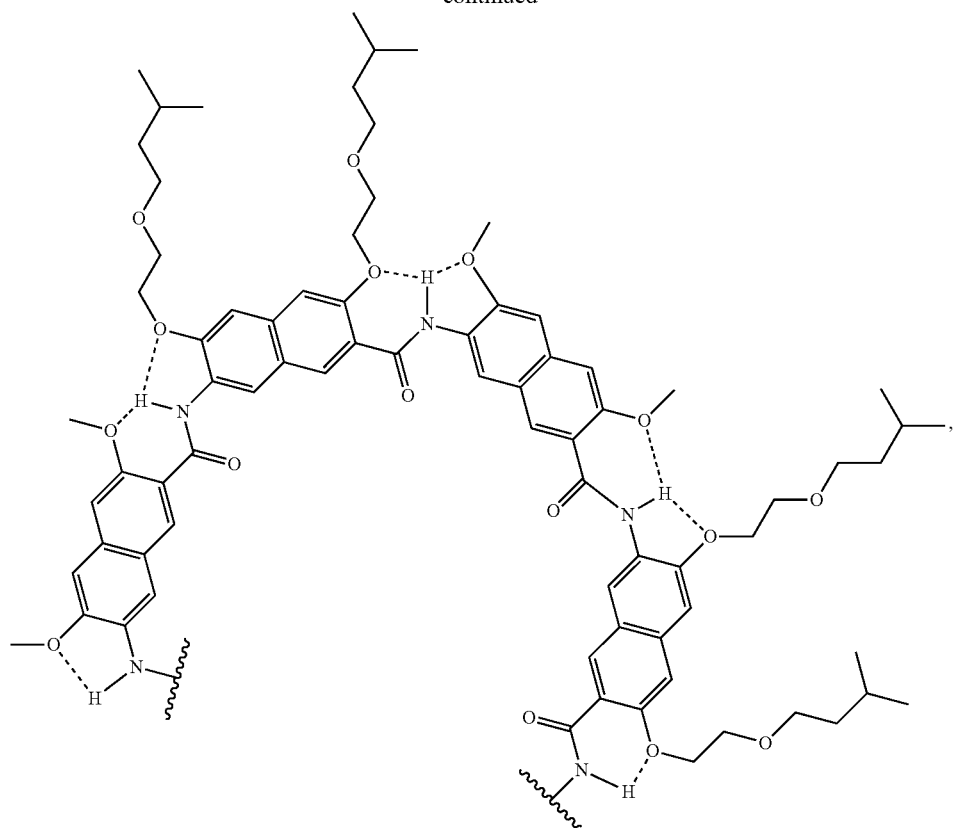
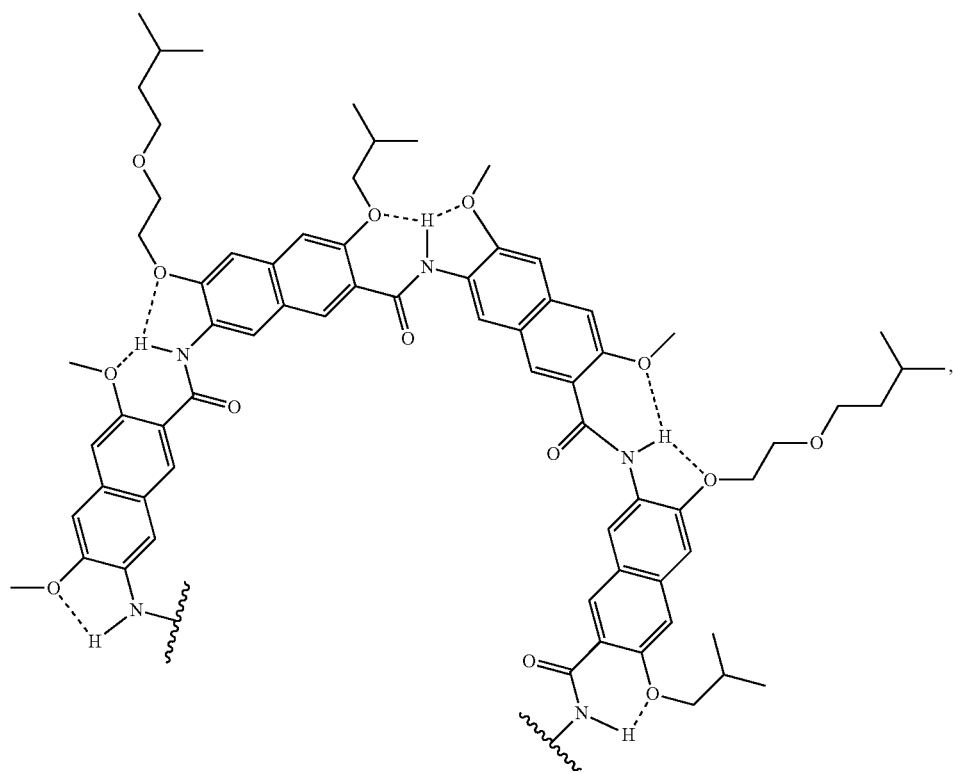

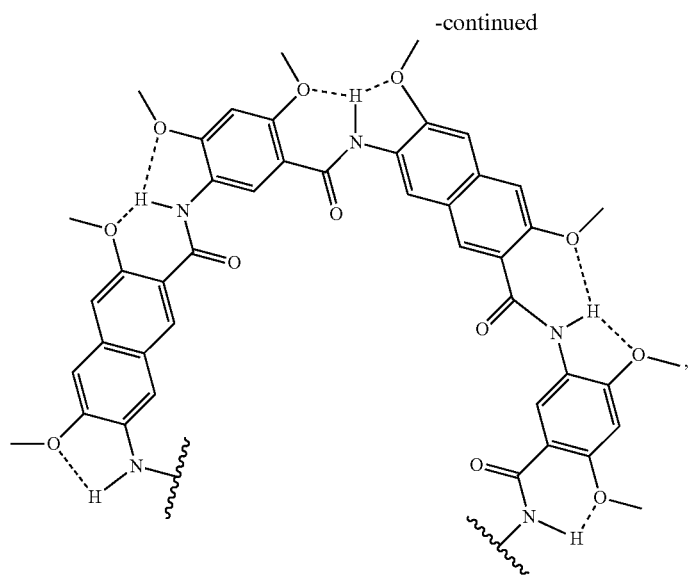
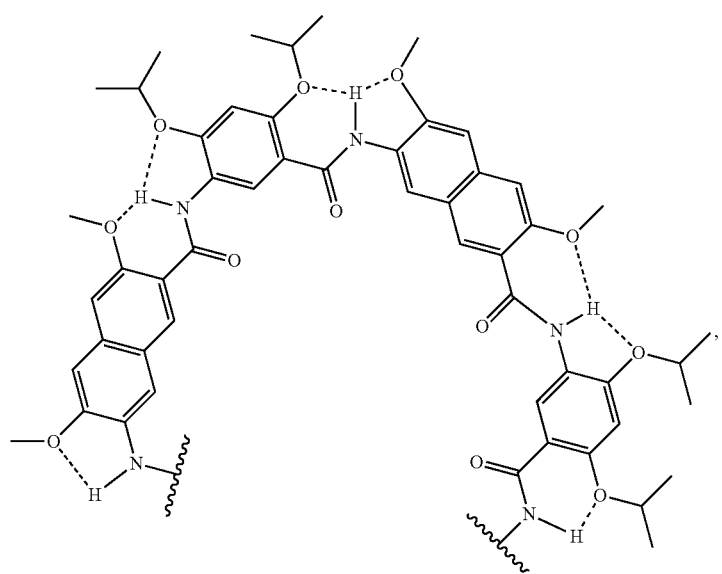

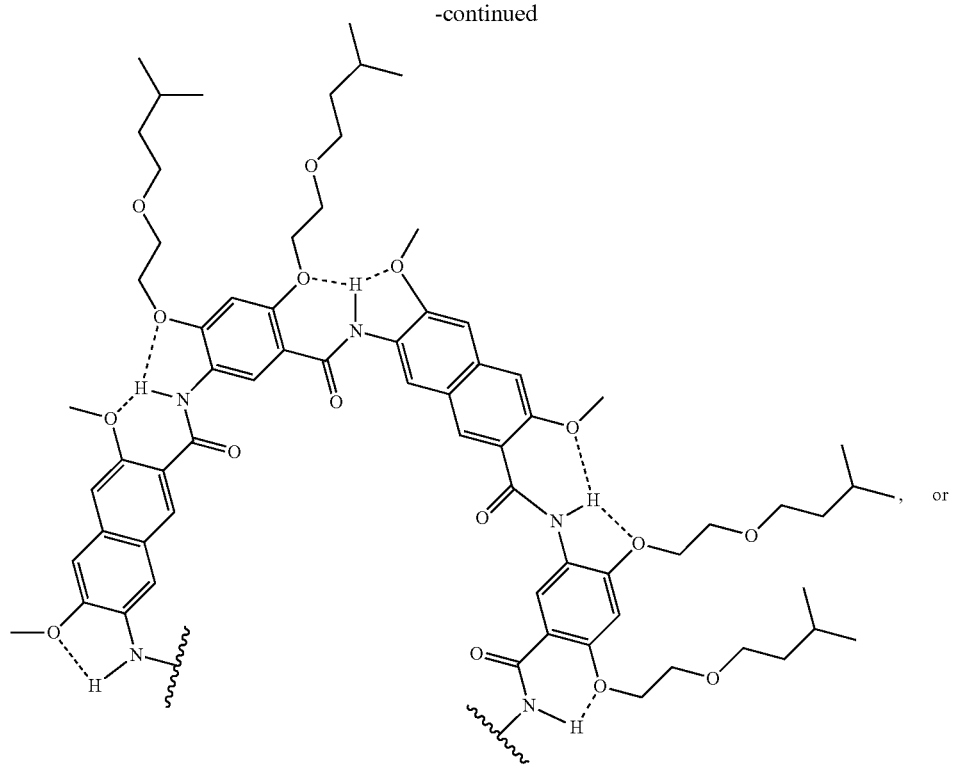
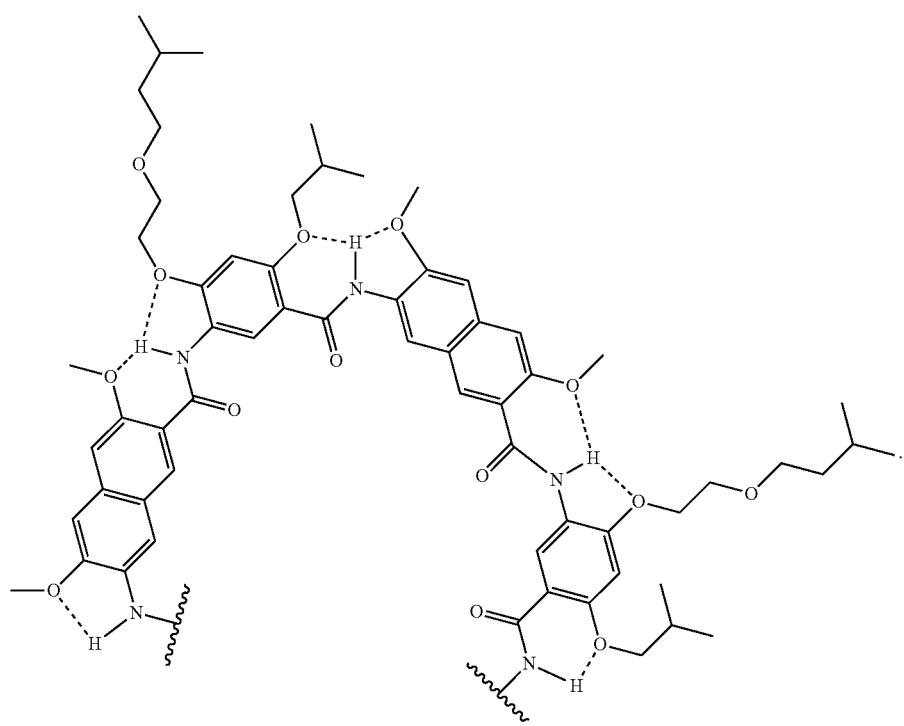
In an example, compounds of the present disclosure form folded, tube-like structures (e.g., a helix). In a non-limiting illustrative example, the compound folds as shown in the following structure (using the B aromatic substituent as an example, and not excluding examples of N, BN, and combinations thereof (including combinations with B)):

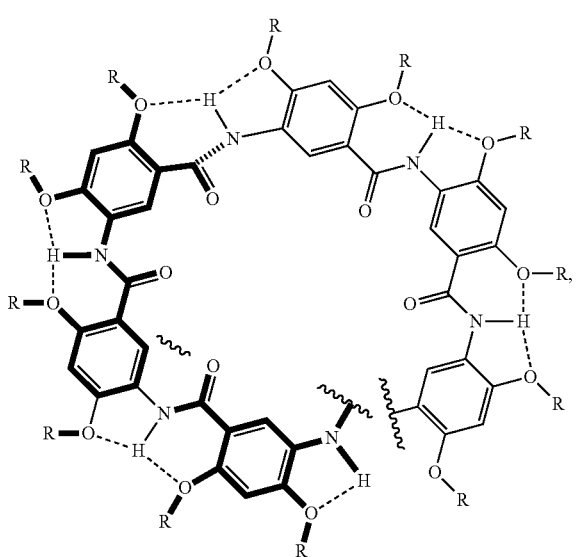

where, moving clockwise from the bolded end of the structure, the compound spirals downward into the page.

A compound of the present disclosure can form a helix (and accordingly can be referred to as a helix or helical compound). A helix can be right-handed or left-handed.

In an example, a helix comprises a compound having 6.5 residues (e.g., a residue is an aromatic substituent having, for example, but not limited to, the structure B, N, BN, or a combination thereof) per turn. A helix can comprise a compound having a pitch of about 3.6 Å per turn. The pitch and number of residues per turn are determined by the bond angles of the aromatic substituents. Not intending to be bound by any particular theory, these bond angles can change by several degrees depending on the temperature. As such, it is expected that the number of residues per turn and the pitch will not be exactly 6.5 residues and 3.6 Å, respectively, but rather the number of residues per turn and pitch will be a range surrounding these base values. For example, a helix can have 6.5±1 residues per turn, including all 0.1 residue values and ranges between 0 and 1. In another example, the helix has a pitch of 3.6±1 Å, including all 0.1 residue values and ranges between 0 and 1.

A helix of the present disclosure has an interior and an exterior portion. In an example, the interior of the helix is a hollow, tubular cavity comprising hydrophilic groups/moieties. In an example, the exterior of the helix comprises hydrophobic groups/moieties.

The interior of the helix has a widest inner linear dimension (e.g., an inner diameter). The widest inner linear dimension of the interior is 3.5 to 15 Å, including all 0.1 Å values and ranges therebetween.

In an example, the widest inner linear dimension (e.g., an inner diameter) can vary in a compound of the present disclosure. In such an example, the helix can comprise different segments, each segment having a different widest inner linear dimension. Such as, for example, one segment of a helix comprising at least one turn can have a widest inner linear dimension of 10 Å. In a second segment of the helix comprising at least one turn can have a widest inner linear dimension of 3.5 Å. In a third segment of the helix comprising at least one turn can have a widest inner linear dimension of 10 Å.

In an example, a helix has a longest linear dimension (e.g., a length). The longest linear dimension is 3.5 to 100 Å, including all 0.1 Å values and ranges therebetween. In another example, the longest linear dimension is 4 to 100 Å, including all 0.1 Å values and ranges therebetween.

It is desirable that the substituents (e.g., R and/or R') on the aromatic substituents are moderately hydrophilic. In an example, a compound of the present disclosure is soluble in a polar, aprotic solvent (e.g., N,N-dimethylformamide (DMF), dimethylsulfoxide (DMSO), and the like). For example, a compound of the present disclosure maintains solubility at a millimolar concentration (e.g., soluble at a concentration 0.1 to 10 mM, including all 0.1 mM values and ranges therebetween).

In an aspect, the present disclosure provides compositions comprising compounds of the present disclosure. In an example, a plurality of compounds of the present disclosure assemble such that the compounds are stacked atop one another to form a cylindrical structure. The cylindrical structure is a composition of assembled compounds and the longitudinal axis of each compound is coaxially aligned. The cylindrical structure has an interior and an exterior. The interior of cylindrical structure is a continuously hollow tubular cavity. Other assemblies are contemplated and are within the scope of the subject invention.

A composition of the present disclosure can form a helix (and accordingly can be referred to as a helix or helical composition). A helix can be right-handed or left-handed.

In an example, a composition comprise helices having 6.5 residues (e.g., a residue is an aromatic substituent having, for example, but not limited to, the structure B, N, or BN) per turn. A helix can comprise a compound having a pitch of about 3.6 Å per turn. The pitch and number of residues per turn are determined by the bond angles of the aromatic substituents. Not intending to be bound by any particular theory, these bond angles can change by several degrees depending on the temperature. As such, it is expected that the number of residues per turn and the pitch will not be exactly 6.5 residues and 3.6 Å, respectively, but rather the number of residues per turn and pitch will be a range surrounding these base values. For example, a helix can have 6.5±1 residues per turn, including all 0.1 residue values and ranges between 0 and 1. In another example, the helix has a pitch of 3.6±1 Å, including all 0.1 residue values and ranges between 0 and 1.

In an example, the interior of the composition comprises hydrophilic groups/moieties. In an example, the exterior comprises hydrophobic groups/moieties.

The interior of a composition of the present disclosure have a widest linear dimension (e.g., a diameter). The widest linear dimension of the interior is 3.5 to 15 Å, including all 0.1 Å values and ranges therebetween.

A composition has a longest linear dimension (e.g., a length). The longest linear dimension is 3.5 to 100 Å, including all 0.1 Å values and ranges therebetween. In another example, the longest linear dimension is 4 to 100 Å, including all 0.1 Å values and ranges therebetween.

In an example, a composition of the present disclosure comprises helical compounds of the present disclosure, where each helical compound has a different longest linear dimension (e.g., a length). Such as, for example, a composition comprises a first compound having a longest linear dimension of 20 Å, a second compound having a longest linear dimension of 9 Å, and a third compound having a longest linear dimension of 4 Å.

In an example, a composition of the present disclosure can comprise helical compounds of the present disclosure, where each helical compound comprises a different plurality of aromatic substituent or combination of pluralities of aromatic substituents. For example, a composition of the present disclosure can comprise a first helical compound comprising BN aromatic substituents, a second helical compound comprising B aromatic substituents, and a third helical compound comprising N aromatic substituents. In another example, a composition of the present disclosure can comprise a first helical compound comprising BN aromatic substituents and B aromatic substituents, a second helical compound comprising BN aromatic substituents, and a third helical compound comprising N aromatic substituents.

In an example, a composition of the present disclosure is soluble in a polar, aprotic solvent (e.g., N,N-dimethylformamide (DMF), dimethylsulfoxide (DMSO), and the like). For example, a composition of the present disclosure maintains solubility at a millimolar concentration (e.g., soluble at a concentration of 0.1 to 10 mM, including all 0.1 mM values and ranges therebetween, in a polar, aprotic solvent).

In an aspect, the present disclosure provides uses of compounds and/or compositions of the present disclosure. In various examples, a compound or compounds and/or composition of the present disclosure are used to form pores in a vesicle (e.g., transmembrane pores in a liposome and/or cell). The pores can be nanopores. In various examples, compounds and/or compositions of the present disclosure can be administered to cells, tissues, organs, or an individual (e.g., an individual in need thereof). The individual may be a human, a non-human mammal, a non-mammalian animal or a plant.

Short helical foldamers (e.g., those having one to five helical turns) can stack atop one another and form self-assembling pores that span a lipid bilayer (e.g., a cell membrane), while long helices (e.g., a single foldamer with up to ten to twelve helical turns) can serve as unimolecular pores that span a lipid bilayer. The self-assembling pores, in particular those consisting of stacked short helices, are stable at low temperature but are disrupted at elevated temperatures due to thermal motion. Such self-assembling pores can be used to develop thermo-responsive (i.e., temperature-responsive) methods for delivering molecules of interest into cells. In an example, the stacked short helices are stable at 1-40° C., including every 0.1° C. value and range therebetween. In various examples, the stacked short helices are stable at 1-37° C., including every 0.1° C. value and range therebetween.

In various examples, compounds and/or compositions of the present disclosure are used in cryoprotection methods, nanopore-facilitated transport and/or uptake of therapeutic and/or diagnostic molecules and/or other pharmaceutical or biological applications. For example, compounds and/or compositions of the present disclosure can be used in methods of delivering drugs (e.g., therapeutic drugs), nutrients, imaging agents, radioactive or fluorescent tracers, or a combination thereof (e.g., as membrane-bound sensor molecules and ions (e.g., in methods for detecting chemical or biological warfare-like toxic proteins and bacteria such as, for example, anthrax)) and as arrays (membranes) of nanopores (which can be used as, for example, materials for or in methods of separation and purification of, for example, molecules and ions).

The compounds and/or compositions of the present disclosure can form transmembrane pores. For example, the membrane is a membrane of a liposome, a cell, or other similar vesicle or molecular system. Compounds and/or compositions of the present disclosure can be referred to as pore-forming compounds and/or compositions.

In an example, a compound and/or composition of the present disclosure forms a unimolecular or self-assembling pore having a length that matches the thickness (typically from ~3.6 to 4.0 nm) of a lipid bilayer or cell membrane. For example, a compound that spans the full length of the membrane is called a molecular pore and/or unimolecular pore. For example, a composition that spans the full length of the membrane is a self-assembled pore.

In an example, a method of the present disclosure comprises contacting (e.g., at temperatures at or below physiological temperature) a compound and/or composition of the present disclosure (e.g., a compound and/or composition of the present disclosure dissolved in a solvent (e.g., water or a mixture of water and one or more polar, aprotic solvent, such as, for example, DMSO or DMF) with a vesicle (e.g., a liposome and/or cell or similar system) having a membrane and so that the compound and/or composition forms a pore that spans the thickness of the membrane (e.g., a transmembrane pore).

A molecule of interest can be transported through a pore (e.g., transmembrane pore) formed by compounds and/or compositions of the present disclosure. In various examples, a molecule of interest is a hydrophilic species. Accordingly, in various examples, a method of the present disclosure comprises contacting a membrane of a vesicle (e.g., a liposome and/or cell or similar system) having a transmembrane pore with a molecule of interest, where the molecule of interest is transported into the vesicle (e.g., a liposome and/or cell or similar system). In various other examples, a molecule of interest (e.g., a hydrophilic species) is transported out of a cell. Non-limiting examples of molecules of interest include ions (e.g., protons, sodium, potassium, or chloride ions), dyes (e.g., 8-hydroxypyrene-1,3,6-trisulfonic acid trisodium salt (HPTS)), nutrients typically used in cell or tissue culture, small molecules (e.g., drugs, such as, for example, the anticancer drug, 5-Fluoro-2'-deoxyuridine (5-FdU), and the like), carbohydrates (e.g., pentoses and hexoses, such as, for example, but not limited to, mannose, glucose, galactose, and the like; disaccharides such as, but not limited to, sucrose and trehalose, and the like), polyhydric alcohols (also referred to herein as "sugar alcohols," such as, for example, mannitol, sorbitol, and the like), sequestration agents of metal ions (e.g., hydrophilic sequestration agents of metal ions, such as, for example, hydrophilic sequestration agents of Fe(II) and/or Fe(III)), cryoprotective agents (CPAs, such as, for example, but not limited to, DMSO, ethylene glycol, and propylene glycol), peptides, and combinations thereof. Examples of suitable CPAs, ions, and nutrients are known in the art.

In various examples, compounds comprising BN and/or N residues are desirable for transporting molecules of interest into or out of cells.

In nanopore-facilitated transport and/or uptake of therapeutic molecules, the applications of the technology may include, but are not limited to: intracellular delivery of drugs (e.g., hydrophilic drugs) and/or adjuvants for biomedical research and applications in biopharmaceuticals for cancer and other diseases; intracellular delivery of antigens, antisense nucleic acids (DNA and RNA) for gene therapy and the like; and other medical applications, such as cell therapy (e.g., chimeric antigen receptor therapy (CAR-T)) and blood therapy.

In example applications, drug delivery and/or drug accessing assistance includes, but is not limited to, delivering one or more drugs or agents (e.g., intracellular delivery of hydrophilic drugs and/or adjuvants) to living organs, non-living organs, specimens, bone marrow, blood, stem cells, etc. of animals (e.g., mammals). The animals may be human or non-human. Example drug delivery applications may include related drug formulations, devices, delivery processes and/or other drug accessing assistance apparatuses or methods.

The technology and related methods may also be used in other pharmaceutical or biological applications, e.g., medical or biomedical applications. Example medical applications may include, but are not limited to, therapy or treatment involving cell therapy (e.g., CAR-T), nucleic acids (DNA/RNA), bone marrow, blood or blood components, gene therapy and the like. Example biomedical applications may include, but are not limited to, biopharmaceutical research for drugs against cancer and other diseases, cell and bacterium freezing, such as *E. coli* and *E. coli* competent cells, *Staphylococcus* and the like.

Non-limiting examples of materials suitable for applications involving compounds and compositions of the present disclosure include mammalian cells (human and non-human), tissues, hybridoma cells, viruses, bacteria, parasites, fungi and the like. Other suitable materials include agricultural or other plants, tissues and cells.

In an example, a molecular and/or self-assembling pore of the present disclosure is used in a method for detection (e.g., as a sensor). The method for detection comprises forming a molecular and/or self-assembling pore in a membrane of a vesicle (e.g., a liposome or similar system) where the vesicle optionally encapsulates a stimuli-responsive molecule (e.g., a fluorescent dye). Without intending to be bound by any particular theory, a molecule of interest (e.g., an analyte, non-limiting examples of an analyte include a carbohydrate, a peptide, a dye, and/or an ion, and the like) is transported into or out of the vesicle where the molecule of interest interacts with or binds to the pore, which disturbs the flow of ions through the pores. The ion transport through the membrane-bound pores is sensed by the encapsulated stimuli-responsive molecules (e.g., florescent dye). The change in local concentration of a molecule of interest is measured by a change in fluorescence emission of the encapsulated stimuli-responsive molecule (e.g., florescent dye).

A method for using compounds and/or compositions of the present disclosure comprises i) contacting a membrane of a vesicle (e.g., a liposome, cell, or similar vesicle or molecular system), where the vesicle optionally encapsulates a stimuli-responsive molecule (e.g., a fluorescent dye), with at least one compound and/or composition of the present disclosure such that the compound and/or composition form a pore in the membrane of the vesicle; ii) contacting an analyte (e.g., a solution comprising an analyte, such as, for example, a carbohydrate, a peptide, a dye, and/or an ion) with the vesicle such that the analyte interacts (e.g., binds) with the pore; and iii) measuring a change in fluorescence emission of the encapsulated stimuli-responsive molecule.

A compound and/or composition of the present disclosure can be used to mediate proton transport (e.g., be used to detect the presence or absence or concentration of protons in a sample). For example, an effective amount of an acid or base (e.g., NaOH) to change the pH of a solution is added a solution comprising a solvent and a vesicle encapsulating a pH-sensitive molecule (e.g., a dye such as, for example, HPTS) or a drug (e.g., a hydrophilic drug such as, for example, 5-FdU) to form a mixture and an amount of a second solution comprising a solvent (e.g., DMSO or DMF) and a compound and/or composition at a millimolar concentration (e.g., 0.1 mM) is added to the mixture. Proton transport is measured by a change in fluorescence emission intensity of encapsulated dye over time.

In an aspect, a compound and/or composition of the present disclosure can be used in a method for molecular-level chromatography.

In an example, transmembrane pores of the present disclosure can be used to selectively transport or deliver a molecule of interest (e.g., a carbohydrate, a peptide, a cryoprotectant agent (CPA), a dye, and/or an ion) into and/or out of vesicle (e.g., a liposome and/or cell or similar system) having a membrane.

In various examples, a molecule of interest used in a method is a cryoprotectant agent (CPA). In biopreservation based on cryoprotection, applications of the technology may include, but are not limited to, preservation of: cells, such as *E. coli* and *E. coli* competent cells, *Staphylococcus* and the like, mammalian cells, hybridoma cells, viruses, tissues, parasites and fungi; plant tissues, seeds, specimens, food, fruits and vegetables and the like; animal tissues, specimens; organs; meat (food), and the like; and human organs, specimens, blood, stem cells and the like.

Example cryopreservation applications may involve delivery of CPAs to cells, tissues and organs of humans, non-human animals, plants, etc. For humans, example cryopreservation applications may include, but are not limited to, delivering CPAs to living organs, non-living organs, specimens, blood (e.g. stem cell) of human beings or the like. For non-human animals, example cryopreservation applications may include, but are not limited to, tissue freezing of non-human animal foods, specimens, organs or the like. For plants, example cryopreservation applications may include, but are not limited to, plant tissue, seeds, specimens, food, fruits and vegetables and the like.

The compound and/or composition are expected to prevent ice formation by facilitating transport of CPAs into cells. The compound and/or composition is/are expected to form unimolecular or self-assembling transmembrane pores that can function as molecular channels to facilitate safe and efficient intracellular delivery and removal of molecules of interest (e.g., CPAs during cryopreservation). These rationally designed synthetic transmembrane pores are expected to serve as selective transmembrane channels to transport molecules of interest. For example, these rationally designed unimolecular and/or self-assembling transmembrane pores are expected to serve as thermo-responsive transmembrane channels to transport CPAs at ≤3° C. when protein channels typically malfunction. The interruption of such transmembrane channels at elevated temperatures (e.g., 37° C.) will prevent the harmful effect of non-selective pores to growing cells. As a result, the cell's CPA exposure time to reach ice-free cryopreservation temperature can be reduced significantly. Post-preservation cell yield and viability will be greatly improved by reducing intracellular ice formation and also by removing non-selective, open channels at temperatures at which cells restore the normal growth.

Compounds and/or compositions of the present disclosure are expected to facilitate the intracellular delivery and transmembrane equilibration of molecules of interest (e.g., CPAs). Size and function tunable, temperature-responsive synthetic transmembrane pores comprising one or more compounds and/or composition of the present disclosure are expected to serve as highly efficient molecular channels, which remain open at subzero temperature to effectively deliver molecules of interest (e.g., CPAs) across the cell membrane. In the case where the molecule of interest is a CPA, this will allow a significant decrease in both the CPA exposure time and loading/unloading temperature during freezing. This temperature-responsive feature, or other engineered environmentally sensitive stimuli, will allow synthetic nanopores to seal off at or above physiological temperature, which offers minimum interference of membrane integrity and low toxicity. This method is expected to be effective when CPA loading in tissues using the "liquidus tracking" or step-wise methods where increasingly concentrated solutions of CPA are loaded in the tissue/organ at progressively decreasing temperatures.

Cryoprotective agents (CPAs) are additives that improve the post-thaw viability of cryopreserved biological systems from cells to large and complex tissues/organs by preventing ice crystal nucleation and growth. Membrane permeable CPAs also prevent osmotic shrinkage of the cells and reduce the volume of available water by penetrating and equilibrating across the cell membrane. All known CPAs exhibit various levels of cytotoxicity at effective concentration which may be decreased by reducing the CPA loading temperature and exposure time. However, most CPAs become effectively impermeable at sub-zero temperatures.

In an example, one or more compounds and/or one or more composition of the present disclosure (which can form synthetic nanopores comprising one or more helical foldamers of the present disclosure) or a composition of the present disclosure are delivered (e.g., administered) into a target system (e.g., a mammalian organ or tissue and mammals and non-human mammals)). Methods of administration are known in the art and non-limiting examples of which are described herein.

In an example, one or more compounds and/or one or more composition of the present disclosure (which can form synthetic nanopores comprising one or more macrocyclic compounds of the present disclosure) are delivered into a target system (such as for example, an organ or tissue (e.g., a mammalian organ or tissue)) at a physiological temperature (e.g., 37° C.), followed by CPA loading at hypothermic temperature (e.g. <4° C.). A high influx rate of CPAs through the nanopores can be maintained during cooling as a function of the concentration gradient across cell membrane, thereby reducing the required time to reach vitrification concentrations. Upon rewarming, the nanopores, especially the self-assembling pores, will be closed due to their increased instability at elevated temperatures. Thus, at or above physiological temperature, the nanopores will seal off, and will diffuse away from the system resulting in low toxicity. This use of synthetic nanopores can significantly reduce toxicity and cell injury due to osmotic shrinkage caused by CPAs and salt during both the cooling and rewarming processes via (1) reducing CPA exposure time and (2) enabling rapid CPA loading at lower temperatures.

Moreover, versatile functional organic nanotubes of diverse sizes and properties by modifying the inner cavities of the helical foldamers allow selective CPA transport while preventing ion exchange. Incorporation of functional supramolecular assemblies to enhance membrane permeability of CPAs could lead to a revolutionary solution to long-term cryopreserve large/complex tissues/organs, which will potentially enable "Organs on Demand."

Compounds and/or compositions of the present disclosure can be provided in pharmaceutical compositions for administration by combining them with any suitable pharmaceutically acceptable carriers, excipients, stabilizers, or a combination thereof. Examples of pharmaceutically acceptable carriers, excipients, and stabilizers can be found in *Remington: The Science and Practice of Pharmacy* (2005) 21st Edition, Philadelphia, Pa. Lippincott Williams & Wilkins. For example, suitable carriers include excipients and stabilizers which are nontoxic to recipients at the dosages and concentrations employed, and include buffers such as, for example, acetate, Tris, phosphate, citrate, and other organic acids; antioxidants including ascorbic acid and methionine; preservatives such as, for example, octadecyldimethylbenzyl ammonium chloride; hexamethonium chloride; benzalkonium chloride, benzethonium chloride; phenol, butyl or benzyl alcohol; alkyl parabens such as, for example, methyl or propyl paraben; catechol; resorcinol; cyclohexanol; 3-pentanol; and m-cresol; amino acids such as, for example, glycine, glutamine, asparagine, histidine, arginine, or lysine; monosaccharides, disaccharides, and other carbohydrates including glucose, mannose, or dextrins; chelating agents such as, for example, EDTA; tonicifiers such as, for example, trehalose and sodium chloride; sugars such as, for example, sucrose, mannitol, trehalose or sorbitol; surfactant such as, for example, polysorbate; salt-forming counter-ions such as, for example, sodium; and/or non-ionic surfactants such as, for example, Tween or polyethylene glycol (PEG). The pharmaceutical compositions may comprise other therapeutic agents. The present compositions can be provided as single doses or in multiple doses covering the entire or partial treatment regimen. The compositions can be provided in liquid, solid, semi-solid, gel, aerosolized, vaporized, or any other form from which it can be delivered to an individual.

Administration of formulations comprising compounds and/or compositions as described herein can be carried out using any suitable route of administration known in the art. For example, the formulations comprising compounds and/or compositions of the present disclosure may be administered via intravenous, intramuscular, intraperitoneal, intracerebrospinal, subcutaneous, intra-articular, intrasynovial, oral, topical, or inhalation routes. The compositions may be administered parenterally or enterically. The compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be clinically needed and/or therapeutically indicated.

The steps of the methods described in the various examples disclosed herein are sufficient to carry out the methods of the present disclosure. Thus, in an example, a method consists essentially of a combination of the steps of the methods disclosed herein. In another embodiment, a method consists of such steps.

In the following Statements, various examples of the compounds, compositions, and methods of using the compounds and compositions of the present disclosure are described:

Statement 1. A compound comprising a plurality of aromatic substituents linked by at least one amide group, where the compound having a curved backbone due at least in part to intramolecular hydrogen bonds that rigidify the amide linkage of each amide group to each aromatic substituent and at least in part to an interaction between the aromatic substituents, whereby the curved backbone is stabilized, where the composition comprises a plurality of aromatic substituents having the structure:

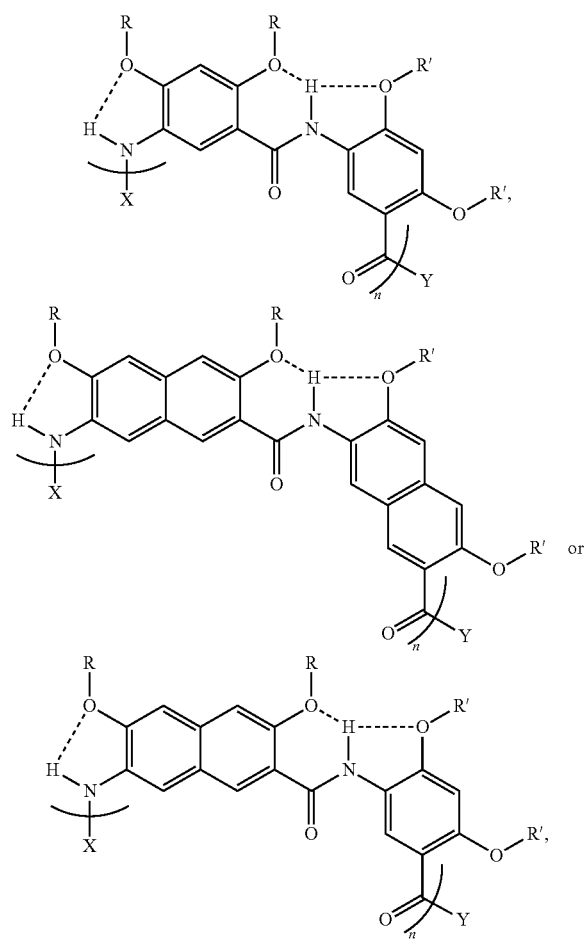

where R and R' are independently at each occurrence selected from the group consisting of linear alkyl (e.g., methyl, ethyl, propyl, butyl, pentyl, hexyl, heptyl, octyl, and the like) groups, branched alkyl groups (e.g., branched derivatives of propyl, butyl, pentyl, hexyl, heptyl, octyl groups, and the like), an ether group, and oligoether group (e.g., —(CH$_2$)$_2$OCH$_3$, —(CH$_2$)$_2$OCH$_2$CH$_3$, —(CH$_2$)$_2$OCH$_2$CH(CH$_3$)$_2$, —(CH$_2$)$_2$O(CH$_2$)$_2$CH(CH$_3$)$_2$,

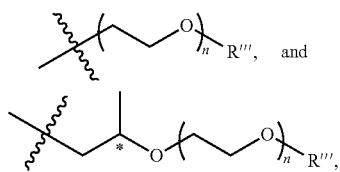

and the like, where the asterisk denotes a stereogenic carbon (i.e., a carbon having R or S stereochemistry), n is 1, 2, 3, 4, 5, or 6, and R''' is a linear or branched alkyl group (e.g., methyl, ethyl, propyl, isopropyl, butyl, isobutyl, t-butyl, pentyl, neopentyl, isopentyl, and the like)), and combinations thereof;

X is an acyl group (e.g., acetyl, trifluoroacetyl, phenylacetyl, fluorenylmethyloxycarbonyl groups, and the like);

Y is:
i) —NHCH$_3$, —NHCH$_2$CH$_3$, —NHR'', and —NHAr; or
ii) —OCH$_3$, —OCH$_2$CH$_3$, —OCH$_2$CH$_3$, —OC(CH$_3$)$_3$, and —OR'', where Ar is an aryl group and R'' is a linear or branched alkyl group (e.g., methyl, ethyl, propyl, butyl, pentyl, hexyl, heptyl, octyl groups, and the like); and n=1 to 64, including all integers and ranges therebetween.

Statement 2. The compound according to Statement 1, where the backbone of the compound folds such that a helix (e.g., left-handed or right-handed helix) is formed (e.g., extending longitudinally in the direction of a longitudinal axis).

Statement 3. The compound according to Statement 2, where there is an interior and an exterior of the helix and the hydrogen bonds are on the exterior of the helix.

Statement 4. The compound according to Statement 2 or 3, where the helix has about 6.5 residues per turn.

Statement 5. The compound according to any one of Statements 2-4, where the helix has a pitch of about 3.6 Å per turn.

Statement 6. The compound according to any one of Statements 3-5, where the interior is a hollow tubular cavity that is parallel to the longitudinal axis.

Statement 7. The compound according to any one of Statements 3-6, where the interior has an inner diameter of 3.5 to 15 Å, including all 0.1 Å value and range therebetween (e.g., 7 to 15 Å).

Statement 8. The compound according to any one of Statements 2-7, where the compound has a length (e.g., a length along the longitudinal axis) of 3.5 to 100 Å, including all 0.1 Å value and range therebetween.

Statement 9. The compound according to any one Statements 3-8, where the interior (also called the inner pore) is hydrophilic and the exterior is hydrophobic.

Statement 10. A helical composition comprising an assembly of the same compounds or a mixture of different compounds according to any one of the preceding Statements, where each compound of the same compounds or the mixture of different compounds is disposed (i.e., stacked) on an adjacent compound (e.g., a longitudinal axis of each compound is coaxially aligned) to form a cylindrical structure.

Statement 11. The helical composition according to Statement 10, where the cylindrical structure has an exterior and an interior.

Statement 12. The helical composition according to Statement 10 or 11, where the interior is a continuously hollow tubular cavity.

Statement 13. The helical composition according to any one of Statements 10-12, where the helical composition has a length (e.g., a length along the longitudinal axis) of 3.5 to 100 Å.

Statement 14. A method of using a compound according to any one of Statements 1-9 and/or a helical composition according to any one of Statements 10-13, comprising forming a transmembrane pore.

Statement 15. The method of Statement 14, comprising contacting a compound according to any one of Statements 1-9 and/or a helical composition according to any one of Statements 10-13 (e.g., a compound and/or a composition dissolved in a solvent, such as, for example, but not limited to, DMSO) with a vesicle having a membrane (e.g., a plasma (or cell) membrane), where the compound and/or the helical composition forms a pore in the membrane.

Statement 16. The method according to any one of Statements 14-15, comprising transporting a molecule of interest (e.g., a hydrophilic compound and/or a hydrophilic species, such as, for example, a carbohydrate, a polyhydric alcohol, a proton, an ion, a dye, a peptide, a CPA, a drug, an adjuvant, or a combination of any of the foregoing) through the pore.

Statement 17. The method according to any one of Statements 14-16, where the contacting comprises administering to an individual (e.g., an individual in need of treatment) the compound and/or the composition.

Statement 18. The method according to Statement 17, where the method further comprises administering a molecule of interest (e.g., a hydrophilic compound and/or a hydrophilic species, such as, for example, a carbohydrate, such as, for example, glucose, sucrose, trehalose, and the like; a polyhydric alcohol, such as, for example, sorbitol, and the like; glycerol; a proton; an ion; a sequestration agent of metal ions (e.g., hydrophilic sequestration agent of metal ions, such as, for example hydrophilic sequestration agent of Fe(II) and Fe(II); a dye; a peptide; a CPA, such as, for example, an antifreeze peptide, a non-natural antifreeze oligomer such as a peptoid, and combinations, and the like; a drug; an adjuvant; or a combination of any of the foregoing) to the individual.

Statement 19. The method according to any one of Statements 14-18, where the method is performed in vivo, in vitro, or ex vivo.

Statement 20. A composition comprising at least one compound according to Statement 1 that forms a continuously hollow tube-like structures for forming pores in membranes, where said pores are stable at low temperatures but are disrupted at elevated temperatures due to thermal motion.

Statement 21. The composition according to Statement 20, where the pores are stable at a temperature of 1 to 40° C., including all 0.1° C. values and ranges (e.g., 1-37° C.).

Statement 22. The composition according to Statement 21 or 22, further comprising a plurality of compounds that are the same or different.

Statement 23. The composition according any one of Statements 20-22, where a plurality of compounds self-assembles into a supramolecular structure.

Statement 24. The composition according to any one of Statements 20-23, where the at least one compound is a helix extending longitudinally in the direction of a longitudinal axis.

Statement 25. The composition according to any one of Statements 20-24, where the helix is right-handed or left-handed.

Statement 26. The composition according to any one of Statements 20-25, where the helix has about 6.5 residues per turn.

Statement 27. The composition according to any one of Statements 20-26, where the helix has a pitch of about 3.6 Å per turn.

Statement 28. The composition according to any one of Statements 20-27, where the composition has a length along the longitudinal axis of 3.5 to 100 Å, including all 0.1 Å value and range therebetween.

Statement 29. The composition according to any one of Statements 20-28, where the tube-like structure has an interior and an exterior.

Statement 30. The composition according to any one of Statements 20-29, where the interior is hydrophilic.

Statement 31. The composition according to any one of Statements 20-30, where the interior is a hollow tubular cavity that is parallel to the longitudinal axis.

Statement 32. The composition according to any one of Statements 20-31, where the interior has an inner diameter of 3.5 to 15, including all 0.1 Å value and range therebetween (e.g., 7 to 15 Å).

Statement 33. The composition according to any one of Statements 20-32, where the exterior of the helix has one or more hydrogen bond.

The following examples are presented to illustrate the present disclosure. They are not intended to limiting in any matter.

Example 1

This example provides a description of oligoamide foldamers and aggregated foldamers of the present disclosure, methods of making same, and characterization of same.

Materials—Aromatic oligoamides having their backbone amide linkages being restricted (or rigidified) with highly favorable intramolecular hydrogen bonds were found to fold into pore-containing helical conformations that are stable in a wide variety of solvents ranging from non-polar to polar solvents including aqueous media. This technology engages in three classes of aromatic oligoamides (FIG. 1) consisting of (1) benzene (B series), (2) naphthalene (N series), and (3) benzene and naphthalene (BN series) residues that fold into helical conformations with hydrophilic inner pores of different diameters based on the same backbone-rigidifying folding mechanism.

The three series of oligoamides fold in the same way, with the helices having ~6.5 residues and a pitch of ~3.6 Å per turn. Due to the different curvatures of their backbones, the helices of each series have inner pores of different diameters. The diameter of the inner pores of the helices of the B series is ~8.5 Å, that of the N series 13 Å, and the BN series 10 Å. The inner pores are chiral and hydrophilic due to the presence of numerous amide oxygen atoms that are helically arranged.

Figure 2:
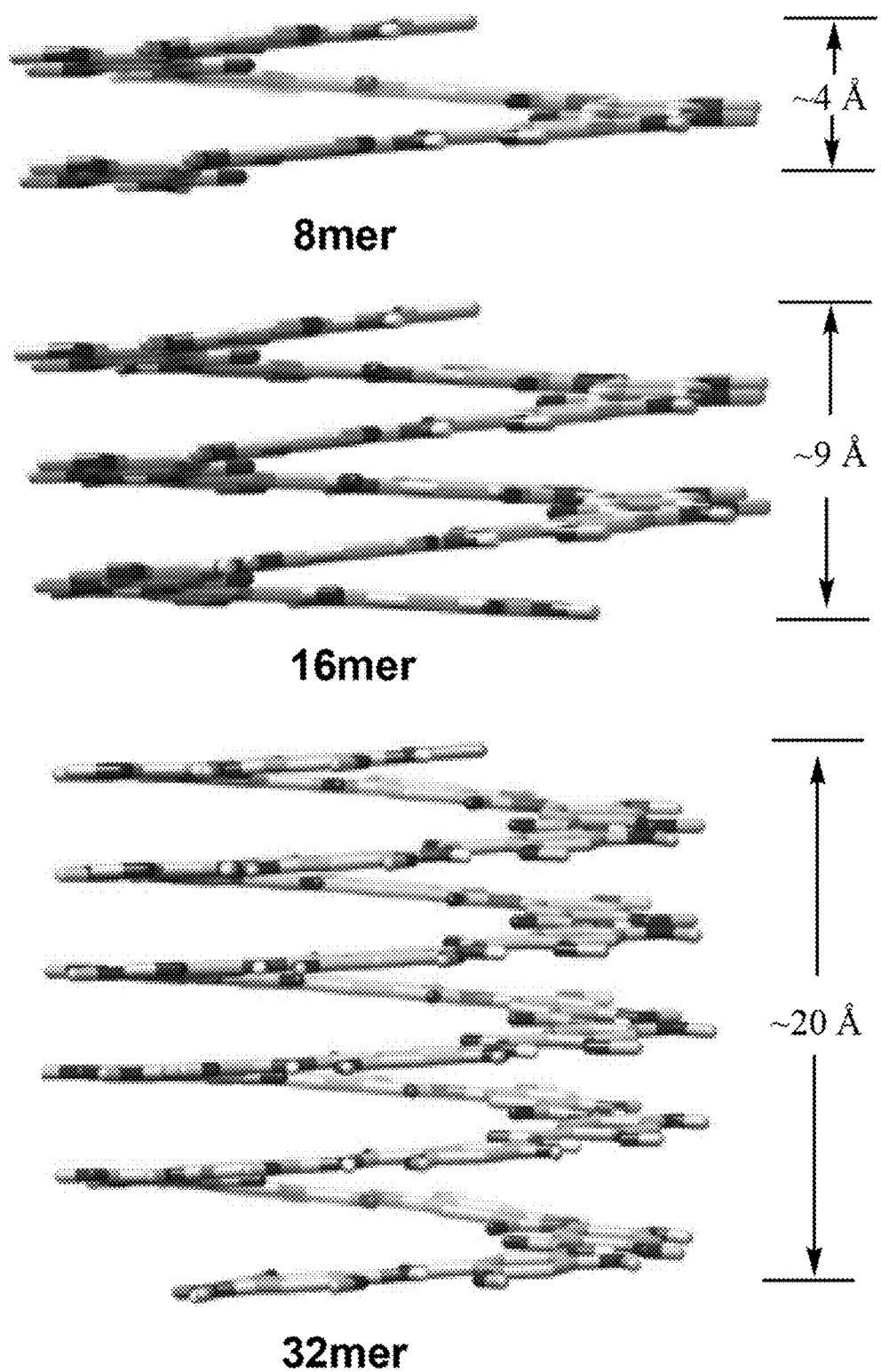
FIG. 2 shows energy-minimized folded structures of (A) the 8mer, 16mer, 32mer, and (B) 64mer of the B series oligomers with all side chains (R groups) being replaced with methyl groups. The approximate length of each helix is shown.
Figure 2:
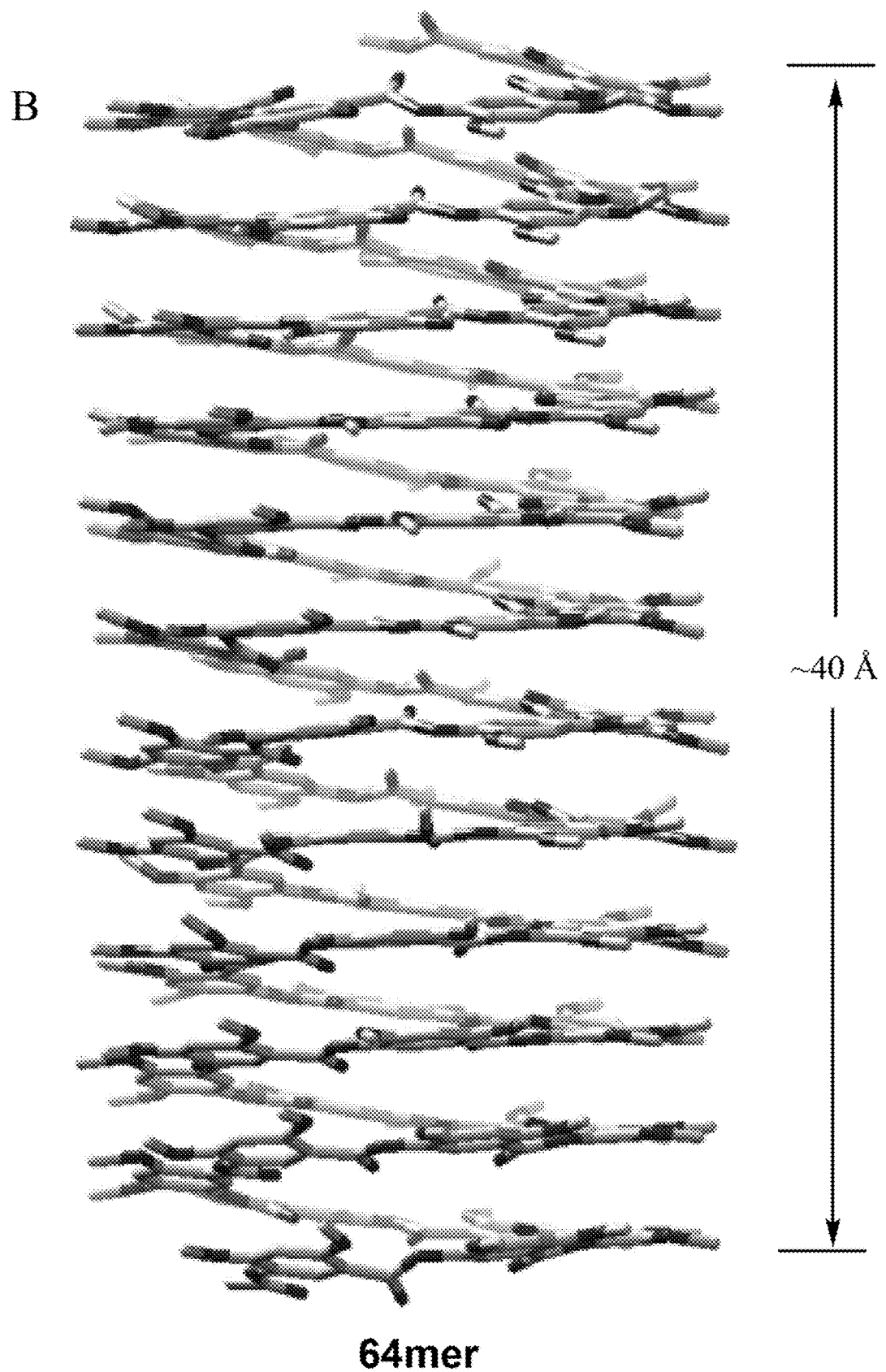

FIG. 2 shows the energy-minimized folded structures of the 8mer, 16mer, 32mer, and 64mer of the B-series oligamides. The length of each of these helices is defined by the chain length (i.e., number of residues) of the corresponding oligomer. Each oligomer of the N and BN series follows the same predictable correlation as shown in FIG. 2 for the B series between its chain length, i.e., its number of monomer residues, and the lengths of the folded helical structure.

Properties and Functions—The transmembrane pore formed by a helix can be a self-assembling one, i.e., a pore that require multiple molecules to stack atop one another to span the membrane; or it can be a molecular one, i.e., one single helix with a sufficient length (~40 Å) is capable of span a lipid bilayer which typically has a thickness of 36 to 40 Å. Among the helices of the B series (and similarly the N and BN series) oligoamides, it takes about eight 8mers, four 16mers, two 32mer, and one 64mer to form a transmembrane pore. Thus only the 64mer is able to serve as a unimolecular pore. Due to entropic reason, the self-assembling pores from 8mer, 16mer, to 32mer are expected to become increasingly stable but will still be less stable as compared to the unimolecular pore of the 64mer. The entropic cost and much more dynamic nature associated with the formation the self-assembling pores, means that such self-assembling pores, especially those formed by the 8mer, will show higher sensitivity toward change in temperature. They will be more stable at low temperature and will be interrupted more frequently with rising temperature. This provide a means to thermal manipulate the open and closed state of the corresponding self-assembling pores.

With their oxygen-decorated hydrophilic inners of different sizes, these three classes of hollow foldamers act as pores that transport cations and hydrophilic molecules (such as various saccharides) across the lipid bilayers (cell membranes). While the diameters of these hydrophilic pores are sufficiently large to allow the passage of cations of essentially all sizes, the different diameters of the three classes of pores will suit the transport of molecules of different. The diameter of the B-series pores allows saccharides with 3-5 carbons and linear sugar alcohols to pass. The BN-series pores have a diameter of ~10 Å and should be able to transport monosaccharides such as glucose, fructose, mannose, and many non-branched di- and oligosaccharides. The N-series helices offer inner pores of ~13 Å across and should allow sucrose, trehalose and oligosaccharides with larger cross sections to pass. These foldamer-based transmembrane pores can thus facilitate the transmembrane transport of biologically important, membrane-impermeable molecules of a variety of range of sizes.

Figure 3:
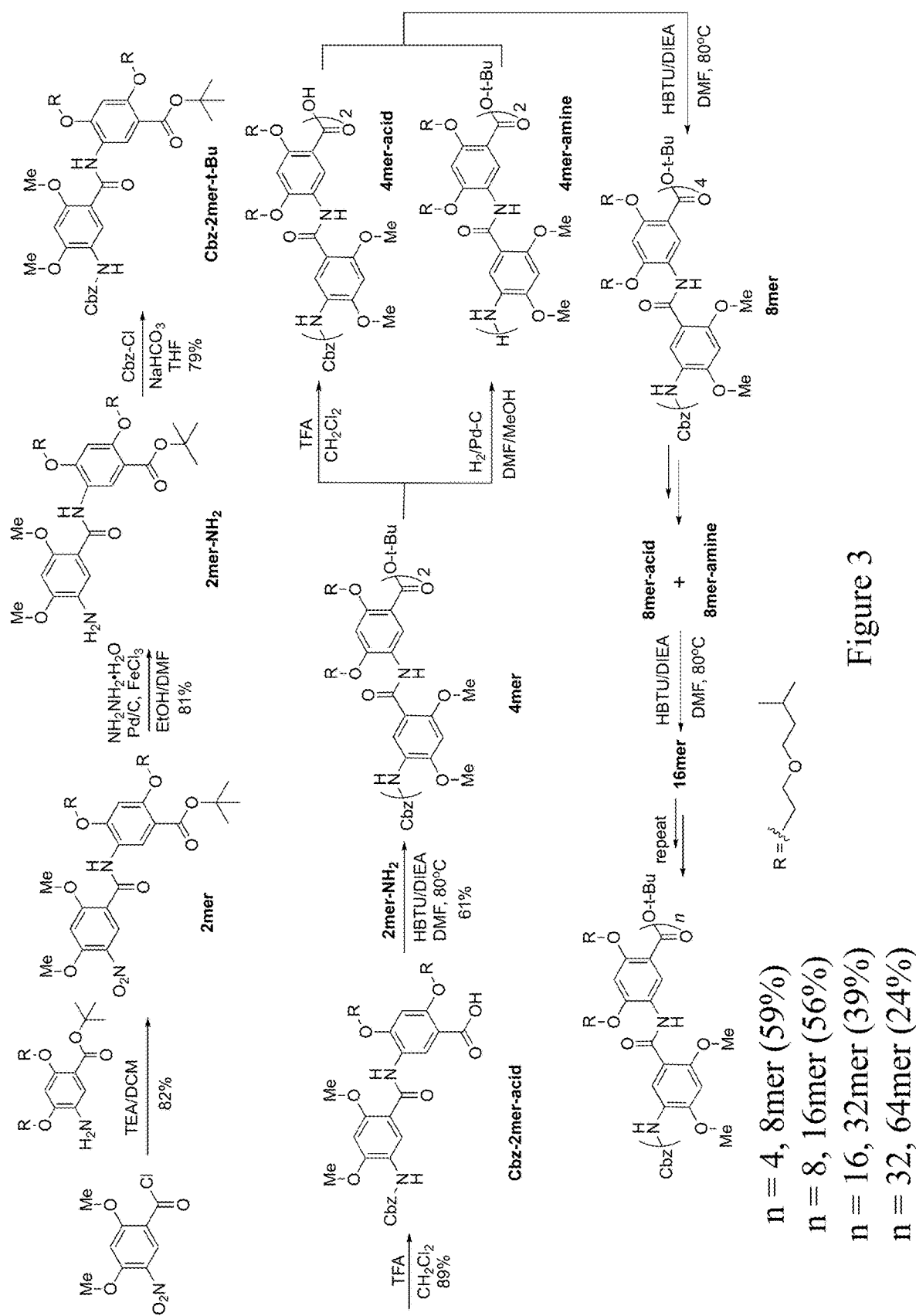
FIG. 3 shows general procedures for synthesizing the B-series oligoamides. The same synthetic steps are equally applicable for the preparation of the N- and BN-series oligoamides.

Methods—Synthesis of aromatic oligoamides. The general procedures for synthesizing the B-series oligoamides is shown in FIG. 3. The same synthetic steps are equally applicable for the preparation of the N- and BN-series oligoamides.

Coupling the monomer acid chloride and amine leads to dimer (2mer) which is reduced to dimer amine (2mer-NH2). Protecting 2mer-NH2 with Cbz group (and similarly with Fmoc or TFA group) followed by removing the t-butyl group results in the dimer acid (Cbz-dimer-acid). Coupling dimer acid with dimer amine with HBTU in DMF at 80° C. gives tetramer (4mer) which is then converted into the 4mer-acid and 4mer-amine. Repeating the same coupling steps gives the octamer (8mer), followed by the 16mer, 32mer, and 64mer. This length-doubling synthetic strategy quickly allows the synthesis of long oligoamides in manageable numbers of coupling steps.

Figure 4:
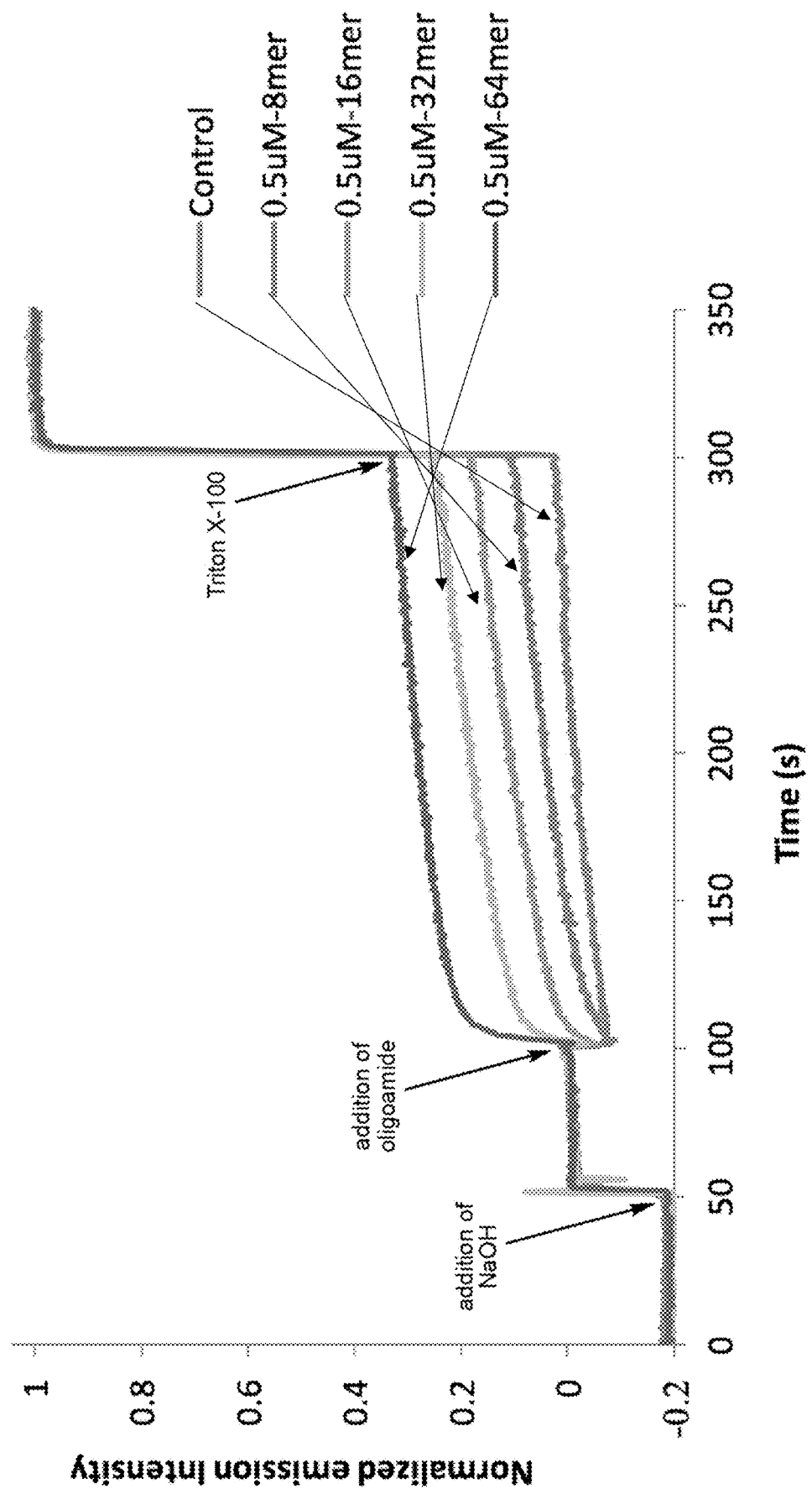
FIG. 4 shows proton transport activities of the B-series oligoamide foldamers.

Transmembrane proton transport mediated by the B-series oligoamide foldamers. The ability of the B-series 8mer, 16mer, 32mer and 64mer to mediated the proton transport across lipid bilayer is assessed with a vesicle-based assay. To a solution of large unilamellar vesicles (LUVs) with encapsulated HPTS, a pH-sensitive fluorescent dye, at pH 7.4 is added an aliquot of 1N NaOH, which increases the pH outside the vesicles and thus creates a proton gradient across the lipid bilayer. An aliquot of a solution (0.1 mM) of one of the oligoamides dissolved in DMSO is added to the solution of the LUVs to reach a final concentration of 0.5 µM, and the time-course of the fluorescence emission of the encapsulated HPTS is followed. Transport of proton out of the LUVs is indicated by an increase in the emission intensity of the encapsulated HPTS. Finally, the detergent Triton X-100 is added to rapture all vesicles, which release the TPTS into the bulk solution. The results are shown FIG. 4.

As expected, all oligomers exhibit noticeable to significant activities in proton transport. The longest 64mer, which should form a unimolecular transmembrane pore, shows the highest activity. The proton transport activities can be directly correlated to the length of the oligoamides, with longer ones show higher activities. Similar trend of transporting other cations and small hydrophilic molecules such as glyceraldehye, glycerol, other linear sugar alcohols such sorbitol, xylitol, etc. can also pass the pores of the B-series oligoamide foldamers and get transported across lipid bilayer.

Example 2

This example provides a description of N-series synthesis.
The following is an example of the synthesis for the N-series monomer having methyl groups is shown in the following scheme:

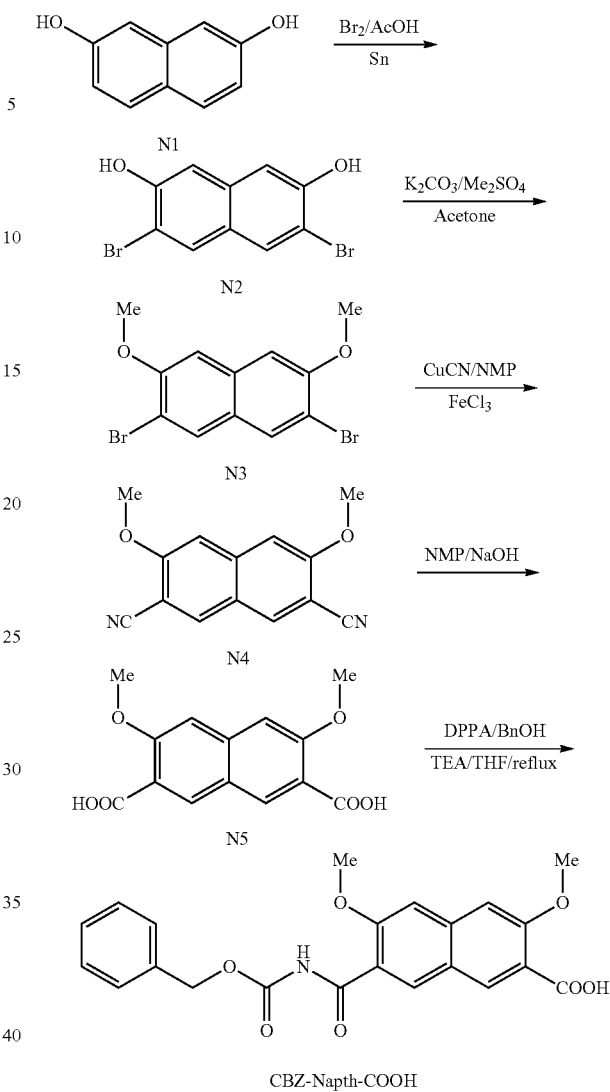

Although the present disclosure has been described with respect to one or more particular embodiments and/or examples, it will be understood that other embodiments and/or examples of the present disclosure may be made without departing from the scope of the present disclosure.

The invention claimed is:
1. A compound having the following structure:

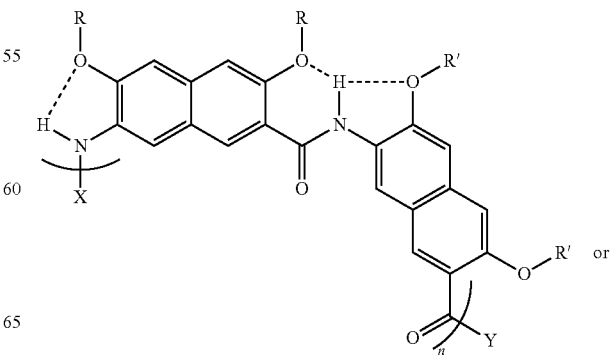

-continued

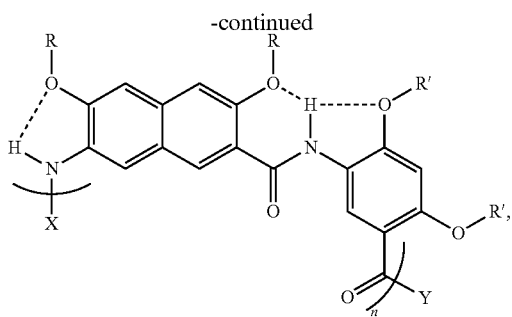

wherein R and R' are independently at each occurrence chosen from methyl groups, ether groups, and oligoether groups;

X is an acyl group;

Y is:
—NHCH$_3$, —NHCH$_2$CH$_3$, —NHR″, —OCH$_3$, —OCH$_2$CH$_3$, —OCH$_2$CH$_3$, —OC(CH$_3$)$_3$, or —OR″, wherein R″ is a linear or branched alkyl group; and n=1 to 64.

2. The compound of claim 1, wherein R and R' are independently at each occurrence

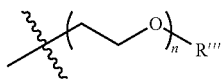

wherein n is 1, 2, 3, 4, 5, or 6, and R‴ is chosen from methyl, ethyl, propyl, isopropyl, butyl, isobutyl, t-butyl, pentyl, neopentyl, and isopentyl.

3. The compound of claim 1, wherein n is 4 to 20 and the backbone of the compound folds such that a helix extending longitudinally in the direction of a longitudinal axis is formed, wherein the helix has a left-handed or right-handed orientation.

4. The compound of claim 3, wherein the helix has about 6.5 aromatic substituents of the compound per turn and/or the helix has a pitch of about 3.6 Å per turn.

5. The compound of claim 3, wherein the helix has an interior and an exterior and the interior is a hollow tubular cavity that is parallel to the longitudinal axis.

6. The compound of claim 5, wherein the interior has an inner diameter of 7 to 15 Å.

7. The compound of claim 3, wherein the helix has a length along the longitudinal axis of 3.5 to 100 Å.

8. A helical composition comprising a plurality of the same compounds of claim 3 or a mixture of different compounds of claim 3, wherein the plurality of the same compounds or the mixture of different compounds are self-assembled such that each of the same compounds or the mixture of different compounds is disposed on an adjacent compound, such that the longitudinal axis of each adjacent compound is coaxially aligned and there is one or more π-π interactions between aromatic substituents of the adjacent compounds, wherein the helical composition has an exterior and an interior.

9. The helical composition of claim 8, wherein the interior is a continuously hollow tubular cavity.

10. The helical composition of claim 8, wherein the helical composition has a length along the longitudinal axis of 3.5 to 100 Å.

11. The compound of claim 1, wherein R and R' are independently at each occurrence

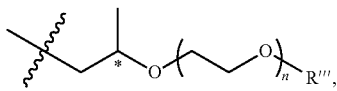

wherein the asterisk denotes R or S stereochemistry, n is 1, 2, 3, 4, 5, or 6, and R‴ is chosen from methyl, ethyl, propyl, isopropyl, butyl, isobutyl, t-butyl, pentyl, neopentyl, and isopentyl.

12. The compound of claim 1, wherein R and R' are independently at each occurrence chosen from ether groups and oligoether groups.

* * * * *